United States Patent [19]

Gunata et al.

[11] Patent Number: 6,106,872
[45] Date of Patent: Aug. 22, 2000

[54] PROCESS FOR OBTAINING AROMA COMPONENTS AND AROMAS FROM THEIR PRECURSORS OF A GLYCOSIDIC NATURE, AND AROMA COMPONENTS AND AROMAS THEREBY OBTAINED

[75] Inventors: Ziya Gunata, Montpellier; Sylvaine Bitteur, Pignan; Raymond Baumes, Gely du Fesc; Jean-Marc Brillouet, Montpellier; Claude Tapiero, Montpellier; Claude Bayonove, Montpellier; Robert Cordonnier, Montpellier, all of France

[73] Assignees: Gist-brocades NV, Ma Delft, Netherlands; Institute National de la Recherche Agronomique (INRA), Paris, France

[21] Appl. No.: 08/062,702

[22] Filed: May 14, 1993

Related U.S. Application Data

[63] Continuation of application No. 07/445,595, Apr. 23, 1990, abandoned, and a continuation of application No. PCT/EP89/00250, Mar. 8, 1989.

[30] Foreign Application Priority Data

Mar. 8, 1988 [FR] France .................................. 88 02961

[51] Int. Cl.[7] .............................. C12G 1/00; C12P 19/44; C12N 9/38
[52] U.S. Cl. .............................. 426/15; 426/51; 435/207; 435/201; 435/74
[58] Field of Search .................................. 426/15, 51, 7; 435/207, 201, 209, 210, 74, 85

[56] References Cited

U.S. PATENT DOCUMENTS

| | | | |
|---|---|---|---|
| 2,950,974 | 8/1960 | Smythe et al. | |
| 4,971,812 | 11/1990 | Tsen | 426/51 |
| 5,573,926 | 11/1996 | Gunata et al. | 435/74 |

FOREIGN PATENT DOCUMENTS

| | | | |
|---|---|---|---|
| 927321 | 5/1963 | United Kingdom | 426/51 |

OTHER PUBLICATIONS

Chemical Abstracts, vol. 75, No. 21, 128 650c (1971).
Journal of Agricultural and Food Chemistry, vol. 26, No. 3, 1978, pp. 765–766.
Parliment et al, "Biogeneration of Aromas", 1986, ACS-:Wash. D.C.: Straus et al, "Role of Monoterpenes in Grape & Wine Flavor," pp. 222–242.
Wilson et al., "Changes in Free and Glycosidically Bound Monoterpenes in Developing Muscat Grapes", *J. Agric. Food Chem.* 32:919–924 (1984).
Engel and Tressl, "Formation of Aroma Components from Nonvolatile Precursors in Passion Fruit" *J. Agric. Food Chem.* 31:998–1002 (1983).
Grossmann et. al., "Enzymatische Freisetzung Gebundener Aromastoffe in Wein", *Deutsche Lebensmittel–Rundschau* 83:7–12 (1987).
Grossman and Rapp, "Steigerung des Sortentypischen Weinbuketts nach Enzymbehandlung", *Deutsche Lebensmittel–Rundschau*, 84:35–37 (1988).
Dubourdieu, et. al., "Role de la Levure Saccharomyces Cerevisiae Dans l'hydrolyse Enzymatique des Heterosides Terpeniques du jus de Raisin", *C.R. Acad. Sci. Paris*, t.306, Serie II, 489–493 (1988).
Darriet, et al., "L'hydrolyse des Heterosides Terpeniques du Muscan a Petits Grains . . . ", *Connaiss Vigne Vin* 22:189–195 (1988).
Aryan et al., "The Properties of Glycosidases of *Vitis vinifera* and a Comparison of Their β–Glucosidase Activity . . . ", *Amer.J. Enol. Vitic.* 38(3):182–188 (1987).
Rapp et al., "Untersuchungen uber der Einfluss der Entsauerung mit Calciumcarbonat . . . " *Vitis* 24(4):241–256 (1985).
Askar and Bielig, "Geschmacksverbesserung von Lebensmitteln", *Alimenta* 15(5):155–159 (1976).
Arana, "Action of a β–glucosidase in the Curing of Vanilla" *Food Research* 8:343–351 (1943).
Ranadive et al.. "Vanillin Biosynthesis in Vanilla Beans" *IXth International Congress of Essential Oils*, Mar. 1983, Singapore, pp. 13–17.
Kodama et al., "Isolation of a New Terpene Glucoside, 3–Hyroxy–5,6–epoxy–β–ionyl–β–D–glucopyranoside from Flue–cured Tobacco" *Agric. Biol. Chem.* 45(4):941–944 (1981).
Marriott, "Biogenesis of Blackcurrant (*Ribes nigrum*) Aroma" *Biogeneration of Aromas*, pp. 185–192 (1986).
Sicard and Fulla, "Utilisation Industrielle des Enzymes pour L'amelioration des Qualites Organoleptiques des Prpduits Alimentaires" *Rivista Italiana EPPO* 59(5):169–181 (1977).
Gunata et al., "Sequential Enzymic Hydrolysis of Potentially Aromatic Glycosides from Grape," *Carbohydrate Research* (1988) 184: 139–149.
Cordonnier et al., *Connaissance De La Vigne Et Du Vin* (1989) 23: 7–23.
Bitteur et al., *J. Sci. Food Agric.* (1989) 47: 341–352.
Brillouet et al., *J. Agric. Food Chem.* (1989) 37: 910–912.
Strauss et al., "Role of Monoterpenes in Grape and Wine Flavor", *Biogeneration of Aromas* (1986) American Chemical Society, Washington, D.C., pp. 222–239.
Pisarnitskii, *Chemical Abstracts* (1971) 75:128650c.
Drawert and Barton, *J. Agric. Food Chem.* (1978) 28:765–766.

*Primary Examiner*—Keith Hendricks
*Attorney, Agent, or Firm*—Morrison & Foerster, LLP

[57] ABSTRACT

An enzymatic hydrolysis of a glycosidic substrate containing at least one of the said precursors is performed with at least one enzyme chosen in accordance with the structure of the said precursor, to liberate the corresponding monoglycosides by cleavage at a glycoside bond, and, in a second stage, an enzymatic hydrolysis of the product of the first stage is performed with at least one enzyme other than or identical to that/those of the first stage and designed to liberate the aroma components and aromas by cleavage of the aglycone-carbohydrate linkage bond. A vegetable material derived from a fruit such as grape or an aromatic or flowering plant, as well as their derivatives and by-products, is chosen as a glycosidic substrate. Terepenols such as geraniol, linalol, nerol and the like, terpene polyols and alcohols such as phenyl ethyl alcohol and benzyl alcohol, or the like, are obtained, in particular, as aroma components or aromas.

14 Claims, 10 Drawing Sheets

PROCESS FOR OBTAINING AROMA COMPONENTS AND AROMAS FROM THEIR PRECURSORS OF A GLYCOSIDIC NATURE, AND AROMA COMPONENTS AND AROMAS THEREBY OBTAINED

CROSS REFERENCE TO RELATED APPLICATIONS

This application is a continuation of U.S. application Ser. No. 07/445,595, filed Apr. 23, 1990 now abandoned, and a continuation of PCT/EP89/00250, filed Mar. 8, 1989.

TECHNICAL FILED

Background

The present invention relates to a process for obtaining aroma components or aromas from their precursors of a glycosidic nature, as well as to the aroma components and aromas obtained by this process.

In some vine varieties, such as muscats, the aroma compounds exist in tow forms, free and bound. The free fraction consists of odoriferous volatile substances, chiefly terpenols. The bound fraction contains precursors of terpenols, especially non-odoriferous diglycosides, formed from α-L-rhamnopyranosyl β- D-glucopyranosides (designated Rha-Glc) and from α-L-arabinofuranosyl β-D-glucopyranosides (designated Ara-Glc), in which the glucopyranosa provides the link between the terpene residue (designated Terp) and the disaccharide, according to the formulae:

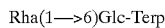
Rha(1—>6)Glc-Terp

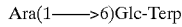
Ara(1——>6)Glc-Terp

The aroma fraction in the form of precursors is most often much larger than the free aroma fraction (typically by a factor of 3 to 10), and it can reach high concentrations, of the order of a few milligrams per liter. Taking into account, in addition, the particularly low threshold of olfactory perception and the aromatic quality of terpene alcohols, there is, in these vine varieties, a most important unexploited aroma potential.

The terpene glycosides, isolated from the juice, may be hydrolyses using commercial enzyme preparations with a wide variety of specifications. The enzymatic liberation of terpenols, which reflects the free natural aroma of the fruit more faithfully than that revealed by thermal hydrolysis at the pH of the juice, is hence possible; however, the control of this liberation for an industrial exploitation of the aroma potential presupposes that the glycosidases responsible for the hydrolyses are defined and their mechanism of action established.

SUMMARY OF THE INVENTION

The present invention is based on a demonstration of the mechanism of enzymatic hydrolysis, such mechanism being of the sequential type.

Thus, the process according to the present invention for obtaining aroma components and aromas from their precursors of a glycosidic nature is characterized in that:

in a first stage, an enzymatic hydrolysis of a glycosidic substrate containing at least one of the said precursors is performed with at least one enzyme chosen in accordance with the structure of the said precursor, to liberate the corresponding monoglucosides by cleavage at a glycoside bond;

in a second stage, an enzymatic hydrolysis of the product of the first state is performed with at least one enzyme other than or identical to that/those of the first stage and designed to liberate the aroma components and aromas by cleavage of the aglycone-carbohydrate link bond.

"Substrate" is understood to mean any substance containing a precursor of a glycosidic nature of an aroma component or aroma.

BRIEF DESCRIPTION OF THE DRAWINGS

1a. Ara-Glc-pNP+β-glucosidase
2a. Ara-Glc-pNP+α-arabinosidase
3a. Ara-Glc-pNP+α-arabinosidase+β-glucosidase
1b. Rha-Glc-pNP+β-glucosidase
2b. Rha-Glc-pNP+α-rhamnosidase
3b. Rha-Glc-pNP+α-rhamnosidase+β-glucosidase

1. Glycosidic extract
2. Glycosidic extract+β-glucosidase
3. Glycosidic extract+α-arabinosidase
4. Glycosidic extract+α-rhamnosidase
5. Glycosidic extract+α-arabinosidase+β-glucosidase
6. Glycosidic extract+α-rhamnosidase+β-glucosidase

a. Silylated glycosidic extract
b. Glycosidic extract+α-arabinosidase
c. Glycosidic extract+α-arabinosidase+β-glucosidase Abbreviations:
I.S. Internal Standard (Glc-pNP)
1 and 2. α- and β-arabinose
5 and 5. α- and β-glucose
a. Glc-Lin
b. Glc-Ner
c. Glc-Ger
A. Ara-Glc-Ner
B. Ara-Glc-Ger
C. Rha-Glc-Ger

A. Ara-Glc-Ner

Figure 1:
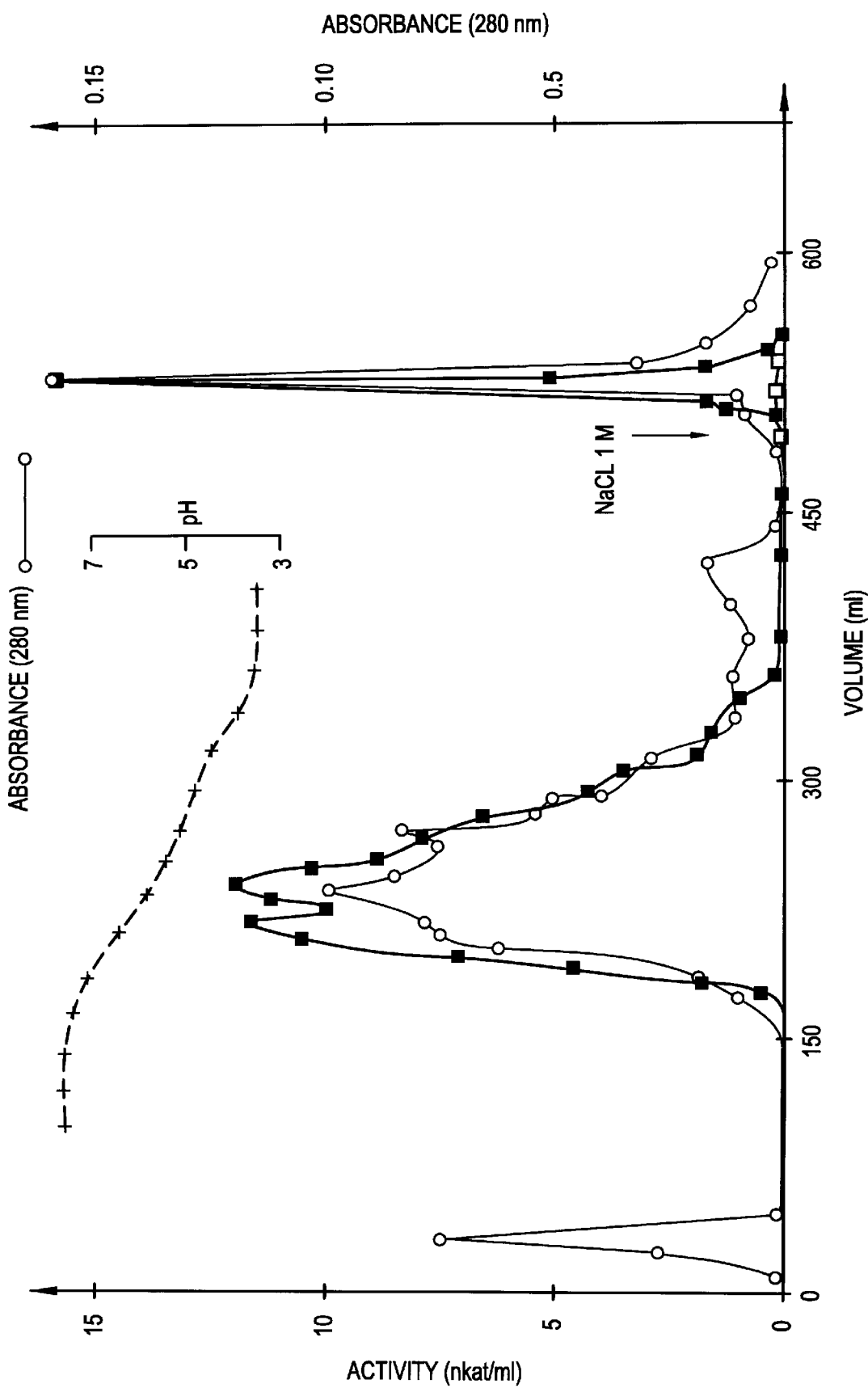
FIG. 1 shows a chromatographic profile of a purification of α-rhamnosidase by chromatic focusing of mariginase of pBE-94 gel.

B. Ara-Glc-Ger.

DESCRIPTION OF THE SPECIFIC EMBODIMENTS

By way of an example, the glycosidic precursor may be a vegetable material derived from grapes, such as grape juices, wines and their derivatives, for example all drinks containing wine, grape juice or a related substance, as well as by-products of the vinification of aromatic vine varieties, especially muscats. The three components of the enzyme system needed for the hydrolysis of the terpene glycosides of grapes to liberate terpenols, odoriferous volatile substances, are now known according to the invention: an α-arabinosidase and an α-rhamnosidase for the first stage, and β-glucosidase for the second stage. The work leading to the present invention has enabled, in effect, to be concluded that the hydrolysis of terpene diglycosides does not proceed from the action of a single glycosidase but, on the contrary of several, obtaining in pairs according to the following two-stage sequential mechanism:

Stage 1: Action of an α-arabinosidase and an α-rhamnosidase, liberating the corresponding terpene monoglucosides by cleavage at the (1—>6) glycoside bond.

Stage 2: Action of a β-glucosidase providing for the liberation of the terpenols by cleavage of the terpene aglycone-carbohydrate link bond.

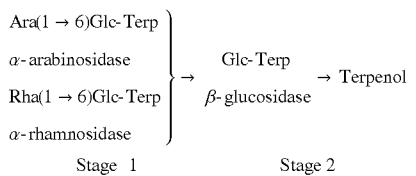

The last key enzyme, namely the β-glucosidase, on which the final liberation of the terpenols depends, must exhibit minimal inhibition by glucose, of activity at acid pH values and with high affinity with respect to the aglycones engaged in the glycosidic substrates, in order for the proposed process to possess complete efficacy in its applications.

According to the invention, the substrates (Ara-Glc-pNP, Rha-Glc-pNP, Ara-pNP, Rha-pNP, Glc-pNP) enabling the activities to be measured, have also been defined, these conditions being essential for the production of the corresponding enzymes.

The process according to the present invention is exemplified by the exploitation of the aroma potential of grapes, the primary plant material being chosen from grape juices, wines and derivatives, as well as by-products of the vinification of aromatic vine varieties, especially but not exclusively muscats.

However, the present invention is not limited to this application. In effect, the mechanism demonstrated is a general mechanism leading to aroma components and aromas which are not necessarily terpenic, and which is applicable to all plant products other than grapes: fruits, fruit derivatives (for example drinks) and fruit by-products; aromatic plants and flowering plants, as well as derivatives and by-products of these plants; other plants such as tea and tobacco; and even plant material originating from in vitro cell cultures; with the following provisos:

(a) that these plant products contain, in sufficient amounts, aroma or perfume precursors of a glycosidic nature, including terpenols and glycosides other than those encountered in grapes, (b) that the specific glycosidases correspond to the structure of the glycosidic precursors; and (c) that the natural medium does not contain inhibitors of the enzymes applied.

As fruits containing glycodides, other than grapes, which can be used in the process of the present invention, apricots, mangos, papayas and passion fruit may be mentioned, inter alia. As a flowering plant, the rose may be mentioned inter alia.

It is also possible to use a glycosidic extract as a glycosidic substrate, or the hydrolysis can alternatively be performed on a natural medium containing the precursors.

Thus, a large number of possibilities are offered for carrying out the process according to the present invention:

working on a natural medium, as described above, the bound aroma is liberated, thereby increasing the aroma of the product itself;

it is also possible to treat a given glycosidic extract (for example of papaya) and to introduce the aroma obtained into another product, for example a drink (grape juice);

it is also possible to introduce one (or more) glycosidic extract(s) (for example papaya extract, marc extract) into a liquid substrate (for example grape juice, natural drinks) and to apply the process according to the invention, thereby liberating the aroma in situ. It is also possible to contrive that the aroma is liberated later, at the desired moment, in a food, a drink or a perfume.

The term "enzyme" defines here any means capable of obtaining the corresponding enzymatic activity. The enzymes employed in the process according to the present invention can be of any origin: bacterial, fungal, yeast, plant, animal or synthetic. Enzymes produced by genetic manipulations using host microorganisms are also encompassed according to the invention.

Microorganism can thus be modified by techniques known to those versed in the art for producing an enzyme or several enzymes, which can be usable in the process.

The process of the invention makes it possible to obtain, in particular as aroma components or aromas, terpenols such a geraniol, linalool, nerol and the like, terpene polyols and alcohols such as phenyl ethyl and benzyl alcohol, or the like.

According to the invention, it is also possible, depending on the profile of the aroma bound to the precursors, which can be different from the free aroma, or depending on the specificity of the enzyme used, to envisage the production of a novel aroma.

Knowledge of the mechanism results in the production of enzymes having novel characteristic properties and technological capabilities.

According to a particular embodiment of the process of the present invention, corresponding to the case where the substrate contains only monoglycosides, the enzymatic hydrolysis is performed directly without passing through the first stage.

In the definition of the invention, as mentioned above, it was stated that the process involved a twostage hydrolysis. However, the invention is in no way limited to the use of two stages with successive additions of separate enzymes. As a variant, it is in effect, perfectly possible, especially if it is the same enzyme or enzymes which liberate(s) the monoglycosides and also the aroma components and aromas, to bring the glycosidic substrate into contact in a single stage with the chosen enzyme or enzymes, the enzymatic hydrolysis then proceeding in at least one reaction phase leading to the desired aromas and/or aroma components. This embodiment of the process of the invention can prove suitable, for example, if at least one microorganism encoded for producing the enzyme or enzymes useful in the reaction is used for the reaction with the glycosidic substrate. In the description which follows, when a first stage and a second stage are referred to in the interest of the convenience of the description, this simply means that the hydrolysis reaction proceeds in several phases, but this in no way means that these reaction phases necessitate separate additions of enzymes.

The present invention will be illustrated by the experimental results reported below:

EXPERIMENTAL

A. THE SUBSTRATES USED

Among the substrates used, p-nitrophenyl β-D-glucopyranoside (Sigma, USA), p-nitrophenyl α-L-arabinofuranoside (Sigma, USA) and p-nitrophenyl α-L-rhamnopyranoside (Extra-synthese, France) are commercially available. The other glycosides were synthesized: their synthesis employs three stages, starting with the corresponding peracetylated saccharide.

The first stage consists in the activation of the anomeric carbon of the terminal carbohydrate group of the peracetylated corresponding saccharide, by introduction, onto this carbon, of a halogen such as chlorine or bromine, or an imidate such as trichloroacetimidate.

Thus, hexaacetyl-α-chlororutinoside is obtained by the action of zinc dichloride and dichloromethyl methyl ether on peracetylated rutin in an inert solvent such as chloroform or methylene chloride, under anhydrous conditions.

Tetraacetyl-α-bromo-D-glucopyranoside and hexaacetyl-α-bromorutinoside are prepared by the action of gaseous hydrobromic acid on pentaaceto-D-glucopyranose and on heptaacetorutinose, respectively, in an inert solvent such as chloroform of methylene chloride, under anhydrous conditions.

The mixture of O-(hexaacetyl α- and -β-rutinosyl) trichloroacetimidates is obtained by the action of hexacetyl-1-rutinose (obtained by the action of benzylamine or ammonia on heptaacetorutinose in an aprotic solvent such as acetonitrile, tetrahydrofuran or ethyl ether) on trichloroacetonitrile, in the presence of a base, for example potassium carbonate or sodium hydride, in an aprotic solvent such as methylene chloride, chloroform or diethyl ether and under anhydrous conditions. O-[Hexaacetyl-6-O-(α-L-arabinofuranosyl)-α- and -β-D-glucopyranosyl] trichloroacetimidates are obtained in the same manner.

The second stage consists in the catalytic nucleophilic substitution of the leaving group introduced, by para-nitrophenol, by a monoterpenol or by an alcohol. Thus, after purification by chromatography on silica gel, a peracetylated β-p-nitrophenyl, β-terpenyl or β-alkyl glycoside is obtained.

Thus, the action of monoterpenols such as geraniol, nerol, α-terpineol or linalol, or of alcohols such as benzyl alcohol or 2-phenylethanol, on peracetyl-α-bromo-D-glucopyranoside or peracetyl-α-bromorutinoside is performed in the presence of silver carbonate, in an aprotic solvent such as, for example, ether, methylene chloride or chloroform, in the presence of drierite or a 0.4 nm (4 Å) molecular sieve; or in the presence of a soluble catalyst such as mercuric cyanide, in acetonitrile, in the presence of a 0.4 nm (4 Å) molecular sieve; the action of p-nitrophenol on peracetyl-α-chlororutinoside is obtained in pyridine, in the presence of silver carbonate and drierite; that of monoterpenols such as linalool, geraniol or α-terpineol on O-(peracetyl-α- and β-rutinosyl) trichloroacetimidates or O-[hexaacetyl-6-O-(α-L-arabinofuranosyl)-α- and β-D-glucopyranosyl] trichloroacetimidates is carried out in the presence of a 0.4 nm (4 Å) molecular sieve and boron trifluoride etherate or para-toluenesulphonic acid in methylene chloride or chloroform.

Chromatography of the desired peracetyl β-glycosides on silica gel is carried out by eluting with ether/pertroleum ether, chloroform/ether, methylene chloride/ether or ethyl acetate/petroleum ether mixtures.

The final stage consists in the removal of the protective acetyl groups from the sugar portion of the glycosides formed; the deacetylation is performed by transesterification in methanol in the presence of a basic catalyst such as sodium methylate.

Among peracetylated saccharides which are the starting materials for these syntheses, only 1,2,3,4-tetra-O-acetyl-6-O-(2,3,5-tri-O-acetyl-α-L-arabinofuranosyl)-β-D-glucopyranose is not commercially available. Its preparation may be accomplished by the synthesis described above, starting with 1,2,3,5-tetra-O-acetyl-α, β-L-arabinofuranose and 1,2,3,4-tetra-O-acetyl-β-D-glucopyranose. However, it is preferable to carry it out by activation of the 1,2,3,5-tetra-O-acetyl-α, β-L-arabinofuranose to 3,5-di-O-acetyl-1,2-O-[(1-exo- and 1-endo-cyano)ethylidene]-β-L-arabinofuranoses using trimethylsilyl cyanide in the presence of a Lewis acid such as stannous chloride, and of the 1,2,3,4-tetra-O-acetyl-β-D-glucopyranose by tritylation to 1,2,3,4-tetra-O-acetyl-6-O-trityl-β-D-glucopyranose. The glycosylation reaction between these two synthons is performed under rigorously anhydrous conditions, in the presence of triphenylcarbonium perchlorate as a catalyst.

It is possible to apply this synthesis to the preparation of p-nitrophenyl 2,3,4-tri-O-acetyl-6-O-(2,3,5-tri-O-acetyl-α-L-arabinofuranosyl)-β-D-glucopyranoside, by coupling the same cyanoethylidene derivative with p-nitrophenyl 2,3,4-tri-O-acetyl-6-O-trityl-β-D-glucopyranoside. However, this glycosylation leads, besides the expected diholoside, to the diholoside having a 1–4 inter-saccharide bond: their separation is possible by chromatography on silica gel, eluting with an ethyl acetate/petroleum ether mixture.

Decaacetyl rutin

In a 500-ml round-bottomed flask equipped with a condenser with a calcium chloride guard tube, 25 g of rutin are added with magnetic stirring to 150 ml of anhydrous pyridine. While the mixture is cooled in a cold water bath, 100 ml of acetic anhydride are then added in the course of approximately 10 minutes, and stirring is continued for 24 hours. The reaction medium is then poured into 1.5 l of ice-cold water: the acetylated derivative precipitates in white crystals. These crystals are filtered off, washed with water and with a little ethyl ether and then dried under vacuum in a desiccator over silica gel. 38.3 g are obtained (yield: 99%)—TLC, silica gel—ether Rf=0.22, m.p. 128–135° C.

2,3,4-Tri-O-acetyl-6-O-(2,3,4-tri-O-acetyl-α-L-rhamnopyranosyl)-α-D-glucopyranosyl chloride Approximately 6 g of $ZnCl_2$ are melted over a Bunsen burner in a crucible. It is allowed to cool under aluminum foil and 4 g of this $ZnCl_2$, which has been coarsely ground, are rapidly placed in a 250-ml round-bottomed flask equipped with a condenser and provided with a calcium chloride guard tube.

The following are then added with magnetic stirring:

80 ml of anhydrous chloroform, then 20 g of decaacetylated rutin;

finally, approximately 20 ml of 1,1,-dichloromethyl methyl ether are introduced in the course of 5 minutes; the mixture is then brought to 75–77° C. for 2 hours.

The chloroform solution is decanted and the pasty residue is washed from the flask with 20 ml of chloroform, and this is combined with the chloroform solution which is evaporated under vacuum in a rotary evaporator at 35–45° C.

The oily yellow residue is taken up in 500 ml of ethyl ether which is washed with ice-cold water, with saturated $Na_2CO_3$ solution and then again with ice-cold water. The organic phase is dried over $Na_2SO_4$ and filtered, and the solution is concentrated in a rotary evaporator under vacuum at about 35° C. The residue, which has partially crystallized, is recrystallized in ethyl ether, and then a second time in anhydrous ethanol. The white crystals obtained are dried under vacuum in a desiccator over silica gel.

6.3 g are obtained (yield—53%)—TLC, silica gel-ether Rf=0.52, m.p. 148–150° C.

p-Nitrophenyl 2,3,4-tri-O-acetyl-6-O-(2,3,4-tri-O-acetyl-α-L-rhamnopyranosyl)β-D-glucopyranoside In an Erlenmeyer equipped with a calcium chloride guard tube and a magnetic stirrer, 3 g of drierite and 1.5 g of p-nitrophenol are introduced into 50 ml of anhydrous pyridine. The mixture is stirred thus for 1 hour, and 5 g of acetochloro-α-rutinoside and 3 g of silver carbonate, freshly prepared and dried, are then added.

Stirring is continued in the dark and at room temperature for 24 hours.

The reaction medium is filtered, the precipitate is washed with a little pyridine and the filtrate is then concentrated in a rotary evaporator under vacuum at about 40–45° C. The residue is taken up twice with 25 ml of benzene and concentrated in the same manner to remove the traces of pyridine. The residue is again taken up in 100 ml of benzene and the solution is washed with ice-cold water, N sodium hydroxide solution and then again with ice-cold water, and finally dried over $Na_2SO_4$. After filtration, the filtrate is concentrated in a rotary evaporator under vacuum at 35–40° C. The reddish, pasty residue is purified by chromatography on silica gel [of a particle size corresponding to passage through a sieve of mesh aperture 67 μm to 199 μm (70 to 230 mesh)], eluting with ethyl ether—Rf=0.5. The purest fractions are concentrated in a rotary evaporator and the white crystals obtained are recrystallized in 95° strength ethanol. 1.4 g are thereby obtained (yield=25%)—TLC, silica gel—ether Rf=0.5, m.p. 185–187° C.

2,3,4-Tri-O-acetyl-6-O-(2,3,4-tri-O-acetyl-α-L-rhamnopyranosyl)-α-D-glucopyranosyl bromide 1.3 g of heptaacetorutinose and 0.4 ml of acetic anhydride in 20 ml of chloroform are placed under nitrogen at −4° C. in a 50-ml round-bottomed flask, and 3.8 ml of a 33% strength solution of gaseous hydrobromic acid in acetic acid are added dropwise. Stirring is continued at −4° C. and 2 hours, and the reaction medium is then poured into 50 ml of ice-cold water. The organic phase is separated after settling has taken place, dried over anhydrous sodium sulphate and concentrated in a rotary evaporator under vacuum at 35° C. The yellow oil obtained is used without purification in the subsequent stage. However, it is possible to crystallize it by taking it up with a little ethyl ether and leaving it in the cold. On filtration under nitrogen, washing with a little ethyl ether and petroleum ether and drying in a desiccator in the cold, 310 mg of white crystals are obtained (yield −23%).

M.p. 120–125° C.

Geranyl 2,3,4-tri-O-acetyl-6-O-(2,3,4-tri-O-acetyl-α-L-rhamnopyranosyl)-β-D-glucopyranoside In a 50-ml round-bottomed flask, the following are stirred for 24 hours under nitrogen at room temperature:

665 mg of bromo-2,3,4-tri-O-acetyl-6-O-(2,3,4-tri-O-acetyl-α-L-rhamnopyranosyl)-α-D-glucopyranoside (crude product of the bromination reaction);

1 ml of geraniol;

0.5 g of mercuric cyanide in 10 ml of acetonitrile.

The mixture is then concentrated in a rotary evaporator under vacuum at 35° C., and the residue is taken up in 50 ml of ethyl ether. The solid which precipitates is filtered off and rinsed with ethyl ether, and the filtrate is concentrated in a rotary evaporator under vacuum at 35° C. The oil residue is chromatographed on silica gel [of a particle size corresponding to passage through a sieve of mesh aperture 67 μm to 199 μm (70 to 230 mesh)], eluting successively with ethyl ether/petroleum ether (10:90) to ether/petroleum ether (75:25) to elute the reutinoside. The fractions containing the rutinoside are combined and concentrated at 35° C. under vacuum in a rotary evaporator. 140 mg of a colourless paste, which it has not been possible to crystallize, are obtained (yield=19%), the product being pure in TLC—silica gel; ether/petroleum ether (3:1) Rf=0.33.

2,3,4-Tri-O-acetyl-6-O-(2,3,4-tri-O-acetyl-α-L-rhamnopyranosyl)-D-glucopyranose

In 100-ml round-bottom flask, a mixture of 600 mg of heptaacetorutinose and 1.2 ml of benzylamine in 80 ml of ethyl ether are left with magnetic stirring and under nitrogen for 24 hours at room temperature. The reaction medium is then concentrated in a rotary evaporator under vacuum, and the oily residue is chromatographed on a column of silica gel [of a particle size corresponding to passage through a sieve of mesh aperture 67 μm to 199 μm (70–230 mesh)], eluting with ethyl ether. The fractions containing hexaacetylrutinose are concentrated in a rotary evaporator under vacuum. 500 mg of colourless oil are obtained (yield=83%); TLC—silica gel—diethyl ether Rf=0.31.

O-[2,3,4-tri-O-acetyl-6-O-(2,3,4-tri-O-acetyl-α-L-rhamnopyranosyl)-α- and -β-D-glucopyranosyl] trichloroacetimidate 2.6 g of 2,3,4-tri-O-acetyl-6-O-(2,3,4-tri-O-acetyl-α-L-rhamnopyranosyl)-D-glucopyranose, 1.6 ml of trichloroacetonitrile and 25 ml of methylene chloride are mixed under nitrogen and at room temperature in a 100-ml round-bottomed flask. 1.6 g of anhydrous potassium carbonate are then added with magnetic stirring, and stirring is continued for 18 hours. The reaction medium is then filtered and the precipitate is rinsed with 10 ml of methylene chloride. The filtrate is concentrated in a rotary evaporator under vacuum at 35° C. and the residue is chromatographed on a column of silica [of a particle size corresponding to passage through a sieve of mesh aperture 67 μm to 199 μm (70–230 mesh)], eluting with a 1:1 ethyl ether/methylene chloride mixture. The fractions containing the imidate are combined and concentrated in a rotary evaporator under vacuum at 35° C. 2.3 g of a colourless oil are obtained (yield=71%); TLC—silica gel—diethyl ether Rf=0.76.

(±)-Linalyl 2,3,4-tri-O-acetyl-6-O-(2,3,4-tri-O-acetyl-α-L-rhamnopyranosyl)-β-D-glucopyranoside In a 100-ml round-bottomed flask, a mixture of 550 mg of (±)-linalool, 650 mg of O-[2,3,4-tri-O-acetyl-6-O-(2,3,4-tri- O-acetyl-α-L-rhamnopyranosyl)-α and -β-D-glucopyranosyl] trichloroacetimidate and 1 g of 0.4 nm (4 Å) molecular sieve in 3 ml of methylene chloride are stirred under nitrogen at room temperature for 30 minutes. 22 µl of a 50% strength solution of boron trifluoride etherate in methylene chloride are then added, and are also added after 40 minutes' magnetic stirring. After a further 40 minutes' stirring, 650 mg of sodium bicarbonate are added to the reaction medium, which is then washed, volume for volume, with 0.5M aqueous sodium bicarbonate solution and then with water. The organic phase is dried over anhydrous sodium sulphate and concentrated in a rotary evaporator under vacuum at 35° C. The oily residue is chromatographed on silica gel [of a particle size corresponding to passage through a sieve of mesh aperture 67 µm to 199 µm (70–230 mesh)], eluting first with a 4:1 petroleum ether/diethyl ether mixture to remove the excess linalool and then with a 1:4 diethyl ether/chloroform mixture to elute the acetylated heteroside. The fractions containing the latter are combined and concentrated in a rotary evaporator under vacuum at 35° C. 190 mg of a colourless oil are obtained (yield=29%); TLC—silica gel; diethyl ether/petroleum ether (4:1) Rf=0.34.

Geranyl 6-O-(α-L-rhamnopyranosyl)-β-D-glucopyranoside

In a 50-ml Erlenmeyer swept with a stream of nitrogen, 0.2 g of geranyl 2,3,4-tri-O-acetyl-6-O-(2,3,4-tri-O-acetyl-α-L-rhamnopyranosyl)-β-D-glucopyranoside are dissolved with mechanical stirring in 2 ml of anhydrous methanol.

0.3 ml of sodium methylate solution (prepared from 230 mg of sodium and 100 ml of anhydrous methanol) is then added in the course of 30 seconds, and stirring is continued under nitrogen in an oil bath at 68–70° C. for 20 minutes. The Erlenmeyer is then cooled in a water/ice bath and approximately 0.2 ml of wet Dowex 50W×4(H$^+$) [of a particle size corresponding to passage through a sieve of mesh aperture 74/147 µm (100/200 mesh)] is added so that the pH of the solution becomes in the region of 7. The resin is then filtered off and the filtrate is concentrated in a rotary evaporator under vacuum at 25° C. The oily residue obtained is purified by chromatography on a column of silica gel 60 [of a particle size corresponding to passage through a sieve of mesh aperture 67 µm to 199 µm (70 to 230 mesh)], eluting with a 3:1 ethyl acetate/methanol mixture. The fractions containing the geranyl β-rutinoside are combined and concentrated in a rotary evaporator under vacuum at 25° C. 110 mg of a colourless paste, which it has not been possible to crystallize, are obtained, the product being pure in TLC—silica gel; ethyl acetate/methanol (3:1) Rf=0.35.

2,3,4-Tri-O-acetyl-6-O-(2,3,5-tri-O-acetyl-α-L-arabinofuranosyl)-α- and -β-D-glucopyranoses Gaseous ammonia is bubbled for 15 minutes into a 100-ml round-bottomed flask containing 25 ml of a 7:3 tetrahydrofuran/methanol mixture and maintained at 0° C. in crushed ice.

400 mg of 1,2,3,4-tetra-O-acetyl-6-O-(2,3,5-tri-O-acetyl-α-L-arabinofuranosyl)-β-D-glucopyranoside are then added.

The flask is then allowed to return to room temperature while stirring is continued.

The reaction is followed by TLC (silica gel; methylene chloride/ether, 6:4). When there is no more starting material (after approximately 15 minutes), the reaction is stopped and the medium is concentrated to dryness under reduced pressure at 40° C.

The residue is then purified on a column of silica, eluting with a 6:4 methylene chloride/ether mixture. 250 mg of product deacetylated at the 1-position are thereby obtained (yield: 67%). TLC—silica gel—methylene chloride/ether (6:4); Rf=0.36.

O-[2,3,4-Tri-O-acetyl-6-O-(2,3,5-tri-O-acetyl-α-L-arabinofuranosyl-α and -β-D-glucopyranosyl] trichloroacetimidate 250 mg of 2,3,4-tri-O-acetyl-6-O-(2,3,5-tri-O-acetyl-α-L-arabinofuranosyl)-α- and -β-D-glucopyranoses, 2.5 ml of absolute methylene chloride, 0.16 ml of trichloroacetonitrile and 160 mg of anhydrous potassium carbonate are introduced into a reactor maintained under nitrogen.

The medium is left for 48 hours at room temperature with magnetic stirring. It is checked that the reaction is complete by TLC (silica gel; methylene chloride/ether, 6:4).

The medium is then taken up with 10 ml of $CH_2Cl_2$ and filtered on a sinter. The organic phase is washed successively, volume for volume, with saturated aqueous $NaHCO_3$ solution and with ice-cold water; it is then dried over anhydrous sodium sulphate and thereafter concentrated to dryness at 35° C. under reduced pressure. 264 mg of a yellowish oil are thereby obtained (yield=88%)—TLC—silica gel—methylene chloride/diethyl ether (6:4)—Rf=0.5.

Geranyl 2,3,4-tri-O-acetyl-6-O-(2,3,5-tri-O-acetyl-α-arabinofuranosyl)-β-D-glucopyranoside 250 mg of O-[2,3,4-tri-O-acetyl-6-O-(2,3,5-tri-O-acetyl-α-arabinofuranosyl)-β-D-glucopyranoside 250 mg of O-[2,3,4-tri-O-acetyl-6-O-(2,3,5-tri-O-acetyl-α-L-arabinofuranosyl)-α- and -β-D-glucopyranosyl] trichloroacetimidates, 250 µl of geraniol and 1.5 ml of anhydrous methylene chloride are introduced into a 50-ml reactor maintained under nitrogen.

The medium is maintained under nitrogen and with magnetic stirring; 20 µl of a 50% strength solution of boron trifuluoride etherate in methylene chloride are added dropwise.

After 3 hours' reaction, it is checked that the reaction is complete by TLC (silica gel, methylene chloride/ether, 7:3), and 50 mg of sodium bicarbonate are then added to the medium. 10 ml of methylene chloride are added and the reaction medium is washed, volume for volume, with ice-cold 0.5M sodium bicarbonate solution and then with ice-cold water. The organic phase is dried over anhydrous sodium sulphate and taken to dryness at 35° C. under reduced pressure. The oily residue is rapidly purified on a column of silica, eluting first the excess geraniol with a 1:1 ether/petroleum ether mixture, and then the product with an 8:2 methylene chloride/ether mixture. 150 mg of a colourless oil are thereby obtained (yield=58%). TLC: silica gel, methylene chloride/ether (8:2), Rf=0.49.

p-Nitrophenyl 2,3,4-tri-O-acetyl-6-O-trityl-β-D-glucopyranoside

In a 100-ml round-bottomed flask, 1.42 g of p-nitrophenyl β-D-glucopyranoside and 1.5 g of anhydrous trityl chloride are introduced into 10 ml of anhydrous pyridine, and the flask is left in the dark with stirring at 40° C. The reaction is followed by TLC, adding trityl chloride if necessary. After 24 hours, the flask is brought to room temperature and 6 ml of acetic anhydride are added. The reaction medium is left for 48 hours with stirring, the reaction being followed by TLC (silica gel, ether/petroleum ether, 7:3); it is taken up in 500 ml of ice-cold water and stirred for 2 hours. The mixture is then filtered through celite and the celite is rinsed with dichloromethane. The organic phase is washed successively with ice-cold water, 10% strength hydrochloric acid, saturated aqueous sodium bicarbonate solution and then ice-cold water. It is dried over sodium sulphate and concentrated under vacuum at 35° C. The residue is chromatographed on a column of silica, eluting with a 7:3 ether/petroleum ether mixture. The fractions containing the heteroside are combined and concentrated under vacuum at 35° C. 2.6 g of an oil are obtained (yield=83%), the product being pure in TLC: silica gel, ether/petroleum ether (7:3), Rf=0.33.

1,2,3,5-Tetra-O-acetyl-α,β-L-arabinofuranose

A mixture of anhydrous L-arabinose (10 g) and anhydrous methanol (200 ml) is treated with 1.06M methanolic hydrochloric acid [prepared by adding acetyl chloride (4.7 ml) and anhydrous methanol (63 ml) at 0° C.]; the mixture is stirred overnight at 0–5° C. Pyridine (40 ml) is added to neutralize the mixture, which is then concentrated. The residue is taken up several times in pyridine, which is removed by distillation, and it is then dissolved in 80 ml of pyridine. Acetic anhydride (30 ml) is added in the cold state, and the solution is left at room temperature for 2 days. Extraction of the reaction medium with ethyl acetate or dichloromethane gives a syrupy product which is then dissolved in a mixture of acetic acid (100 ml) and acetic anhydride (25 ml); 5 ml of concentrated sulphuric acid are added at 0° C., and the mixture is left overnight at room temperature. The solution is then immersed in crushed ice (150 g) and the mixture is stirred for 2 hours and then extracted with chloroform. The extract is washed with water and then with aqueous sodium bicarbonate solution; the residue obtained after concentration of the organic phase is chromatographed on a column of silica gel (eluant:benzene/ether gradient) and gives 1,2,3,5,-tetra-O-acetyl-α,β-L-arabinofuranose in the form of a syrup (18 g, 85%), Rf=0.46 (eluant:benzene).

3,5-Di-O-acetyl-1,2-O-[1-exo- and 1-endo-cyano) ethylidene]-β-L-arabinofuranose

Anhydrous stannous chloride (360 mg) and trimethylsilyl cyanide (3 ml) are added to a solution of 1,2,3,5-tetra-O-acetyl-α,β-L-arabinofuranose (3 g) in acetonitrile (10 ml). The mixture is stirred overnight at room temperature, then diluted with ether and washed with aqueous sodium bicarbonate solution (3×75 ml) and then with water. The organic phase is concentrated and the residue is chromatographed on a column (eluant:benzene/ether gradient) to give the 1-exo-cyano (994 mg; 37%) and 1-endo-cyano (700 mg; 26%) product. Crystallization with ether/pentane gives the 1-exo-cyano isomer (35%), m.p. 66–69° C., [α]$_D$-6° (C1), Rf=0.56 (eluant:benzene/ether, 3:2). Crystallization with toluene gives the 1-endo-cyano isomer (25%), m.p. 107–110° C., [α]$_D$+51° (C1), Rf=0.37.

1,2,3,4-Tetra-O-acetyl-6-O-(2,3,5-tri-O-acetyl-α-L-arabinofuranosyl)-β-D-glucopyranose and p-nitrophenyl 2,3,4-tri-O-acetyl-6-O-(2,3,5-tri-O-acetyl-α-L-arabinofuranosyl)-β-D-glucopyranoside Into two round-bottomed flasks closed and joined by a tube shaped like a tuning-fork, there are introduced, on the one hand (in one flask) a solution of tritylated glucoside (0.55 mmol) and 3,5-di-O-acetyl-1,2-O-[(1-exo- and 1-endo-cyano)ethylidene]-β-L-arabinofuranose (0.5 mmol) in nitromethane (2 ml), and on the other hand (in the other flask) a solution of triphenylcarbonium perchlorate (0.05 mmol) in 0.2 ml of nitromethane. Both solutions are lyophilized, and then 2 ml of distilled benzene are introduced into each flask, the contents being lyophilized again; the operation is repeated a second time; the flasks and the reactants are thus dried over several hours. Dichloromethane (2 ml) is distilled in situ into each of the two flasks. The two solutions are then combined and left to react overnight at room temperature and in the dark [the lyophilization and also the drying of the reactants, as well as the distillation of a benzene and dichloromethane over CaH$_2$, are performed at a pressure of 0.533 pa (4×10$^{-3}$ mmHg)]. The brilliant yellow reaction medium is treated with 1 ml of pyridine/water (3:1), and the decolorized solution is then diluted with chloroform (50 ml), washed with water (3×30 ml) and concentrated. The residue is purified on a column of silica gel, eluting with benzene/ether or ethyl acetate petroleum ether gradient, to yield:

from 1,2,3,4-tetra-O-acetyl-6-O-trityl-β-D-glucopyranose, 1,2,3,4-tetra-O-acetyl-6-O-(2,3,5-tri-O-acetyl-α-L-arabinofuranosyl)-β-D-glucopyranose, m.p. 106.5–108.5° C. (ether/pentane); TLC: silica gel; benzene/ether (3:2), Rf=0.35.

from p-nitrophenyl 2,3,4-tri-O-acetyl-6-O-trityl-β-D-glucopyranoside, p-nitrophenyl 2,3,4-tri-O-acetyl-6-O-(2,3,5-tri-O-acetyl-α-L-arabinofuranosyl)-β-D-glucopyranoside; TLC: silica gel; ethyl acetate/petroleum ether 1:1, Rf=0.24 and p-nitrophenyl 2,3,6-tri-O-acetyl-4-O-(2,3,5-tri-O-acetyl-α-L-arabinofuranosyl)-β-D-glucopyranoside; TLC, silica gel; ethyl acetate/petroleum ether (1:1), Rf=0.28.

Gernayl 6-O-(α-L-arabinofuranosyl)-β-D-glucopyranoside 200 ml of geranyl 2,3,4-tri-O-acetyl-6-O-(2,3,5-tri-O-acetyl-α-L-arabinofuranosyl)-β-D-glucopyranoside are dissolved under nitrogen in 5 ml of anhydrous methanol with magnetic stirring. 0.1 ml of a methanolic solution of sodium methylate (prepared from 20 mg of sodium and 10 ml of methanol) is added. Stirring is continued for 4 hours at room temperature, and the solution is then neutralized by adding Dowex 50W×4 (H$^+$) resin.

The mixture is filtered and the solution is concentrated to dryness in a rotary evaporator. The oily residue is purified by chromatography on a column of silica gel, eluting with an 8:2 chloroform/methanol mixture to yield 105 mg of geranyl 6-O-(α-L-arabinofuranosyl)-β-D-glucopyranoside in the form of a syrup. Yield 81%, TLC: silica gel, chloroform/methanol (8:2), Rf=0.17.

p-Nitrophenyl 6-O-(α-L-arabinofuranosyl)-β-D-glucopyranoside

By deacetylation of p-nitrophenyl 2,3,4-tri-O-acetyl-6O-(2,3,5-tri-O-acetyl-α-L-arabinofuranosyl)-β-D-glucopyranoside according to the above procedure, p-nitrophenyl 6-O-(α-L-arabinofuranosyl)-β-D-glucopyranoside is obtained. TLC: silica gel, ethyl acetate/isopropanol/water (65:30:10), Rf=0.69.

B. MEASUREMENT OF THE ENZYMATIC ACTIVITIES AND PURIFICATION OF THE ENZYMES

1—Measurement of the enzymatic activities

The glycosidase activities are determined by incubating 0.1 ml of 4 mM substrate (Glc-pNP, Ara-pNP, Rha-pNP) in a 100 mM acetate buffer (pH 4.2) with 0.1 ml of enzyme solution at 40° C. for 20 minutes. The liberation of pNP is estimated by adding 0.6 ml of 1M sodium carbonate to the incubation medium and then measuring the optical density at 400 nm. 1 nkat of activity corresponds to the liberation of 1 nmol of pNP per second.

Two glycosidases, α-arabinosidase and α-rhamnosidase, were isolated and purified from commercial preparations containing complex mixtures of enzymes.

Sweet almond β-glucosidase (Koch-Light, Great Britain, Batch No. 2872-01), not displaying any α-arabinosidase and α-rhamnosidase type contaminant activity (24 h of incubation at 40° C., pH 4.2), was used without further purification.

2—Purification of the enzymes 2-1. Purification of an α-L-rhamnopyranosidase

The α-rhamnosidase was purified from naringinase (Sigma) rich in these activities. The β-glucosidase activities, although low (0.1% of the α-rhamnosidase activity), but capable of liberating glucose over long incubation periods, were removed by the technique of chromatofocusing.

The experimental protocol:

Purification of α-rhamnosidase by chromatofocusing of naringinase on PBE 94 gel 50 mg of naringinase, taken up in 4 ml of 25 mM imidazole buffer (pH 7.4), are dialysed against the same buffer (25 ml) overnight (5° C.) The dialysate is injected onto a column (1.0×40 cm) of ion exchanger (Polybuffer exchanger PBE 94, Pharmacia, Sweden) equilibrated with the same buffer. The proteins bound to this gel are eluted by a pH gradient from 7.4 to 3.7, created during the migration of Ampholines [Polybuffer 74 (Pharmacia) adjusted berforehand to pH 3.7]at a flow rate of 44 ml/h.

After the gradient is completed, the passage of 1M NaCl in 100 mM acetate buffer (pH 3.7) desorbs the proteins retained.

2.8-ml fractions are collected, on which the α-rhamnosidase and β-glucosidase activities, the pH and the optical density at 280 nm are measured.

The chromatographic profile is shown in FIG. 1, to which the legend is as follows:

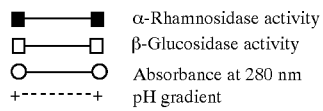

■————■ α-Rhamnosidase activity
□————□ β-Glucosidase activity
○————○ Absorbance at 280 nm
+--------+ pH gradient The α-rhamnosidase activities are eluted in the pH gradient, whereas the whole of the β-glucosidase activity is retained up to pH 3.7 (pI<3.7) and eluted by the passage of a 1M NaCl solution.

This technique shows that naringinase contains at least 3 (rhamnosidase) isoenzymes of isoelectric points pI 6.2, pI 5.7 and pI<3.7. the second (317 nkat/ml), showing no residual β-glucosidase activity even after more than 24 hours' incubation at 40° C. is chosen for the tests of enzymatic hydrolysis of natural and synthetic glycosides.

The overall recovery yield of the α-rhamnosidase activities is approximately 62%.

2—2. Purification of an α-L-arabinofuranosidase

Among the commercial enzyme preparations studied, Hemicellulase REG-2 (Gist Brocades, France) proved rich in α-arabinosidase activity. Nevertheless, it displays substantial activities of the β-glucosidase and α-rhamnosidase type. For example, 250 mg of Hemicellulase contain 2,327 nkat of α-arabinosidase activity, 2,566 nkat of β-glucosidase activity and 236 nkat of α-rhamnosidase activity. Several chromatographic techniques are applied successively in order to isolate and purify the α-arabinosidase.

Molecular sieving of Hemicellulase on Ultrogel AcA 44 Fractionation

The enzyme solution (250 mg of Hemicellulase in 3 ml of 100 mM citrate-phosphate buffer, pH 7.2) is dialysed against the same buffer (500 ml) overnight (+5° C.). The dialysate is then placed on a column (1.6×100 cm) of Ultrogel AcA 44 (IBF, France) equilibrated beforehand with the same buffer. The column is then eluted with the above buffer at a flow rate of 9 ml/h. 1.2-ml fractions are collected and the α-arabinosidase, β-glucosidase and α-rhamnosidase activities, as well as the optical density at 280 nm, are measured.

Results

Figure 2:
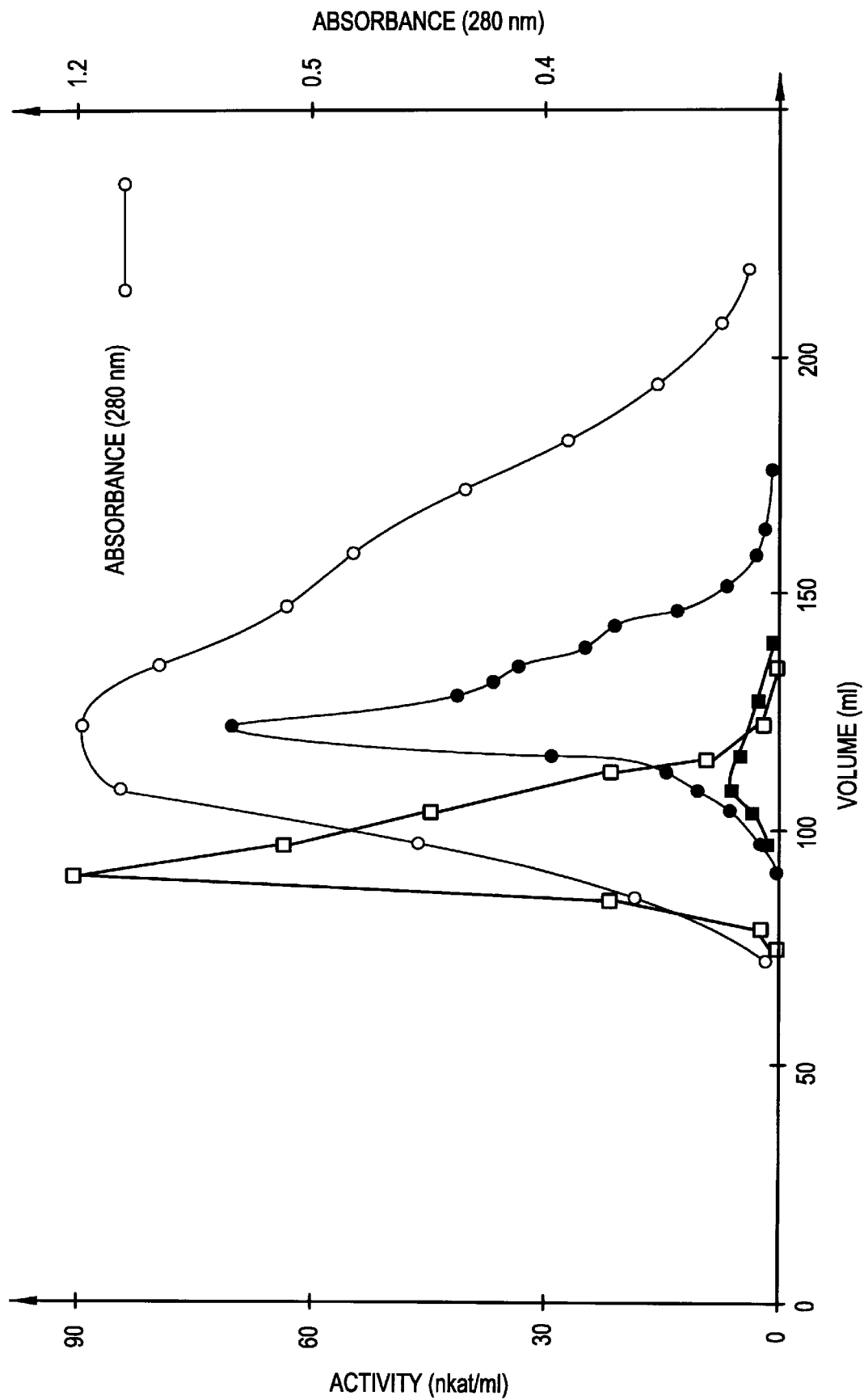
FIG. 2 shows a chromatographic profile of a purification of α-L-arabinofuranosidase on Ultrogel AcA44.

The chromotographic profile is shown in FIG. 2, the legend to which is as follows:

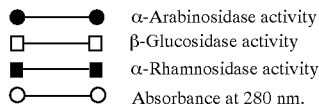

●————● α-Arabinosidase activity
□————□ β-Glucosidase activity
■————■ α-Rhamnosidase activity
○————○ Absorbance at 280 nm.

Molecular sieving on Ultrogel AcA 44 enables the two major α-arabinosidase and β-glucosidase activities to be separated. The α-rhamnosidase activities are co-eluted with the α-arabinosidase activities. The majority of the proteins present in the initial enzyme solution is eluted with the α-arabinosidase activities.

The fraction (52 ml) corresponding to the α-arabinosidase activities (1,750 nkat) also contains trace activities, that is to say β-glucosidase (23.4 nkat) and α-rhamnosidase (37.4 nkat), equivalent to 1.3% (β-glucosidase) and 2.1% (α-rhamnosidase) relative to the α-arabinosidase activity.

Ion exchange chromatography on DEAE-Sepharose CL-6B of the α-arabinosidase fraction derived from the molecular sieving Fractionation The α-arabinosidase-rich fraction (52 ml) was dialysed against 500 ml of 25 mM imidazole-HCl buffer (pH 7.5) overnight (+5° C.) the dialysate is then placed on a column (1.6×40 cm) of DEAE-Sepharose CL-6B (Pharmacia) equilibrated beforehand with the same buffer. The gel is first washed with this buffer at a flow rate of 108 ml/h. The proteins retained on the column are then eluted by a linear gradient of sodium chloride (from 0 to 0.4M) in the same buffer (imidazole-HCl) at a flow rate of 40 ml/h. 4-ml fractions are collected, on which the α-arabinosidase, β-glucosidase and α-rhamnosidase activities and the optical density at 280 nm are measured.

Results

Figure 3:
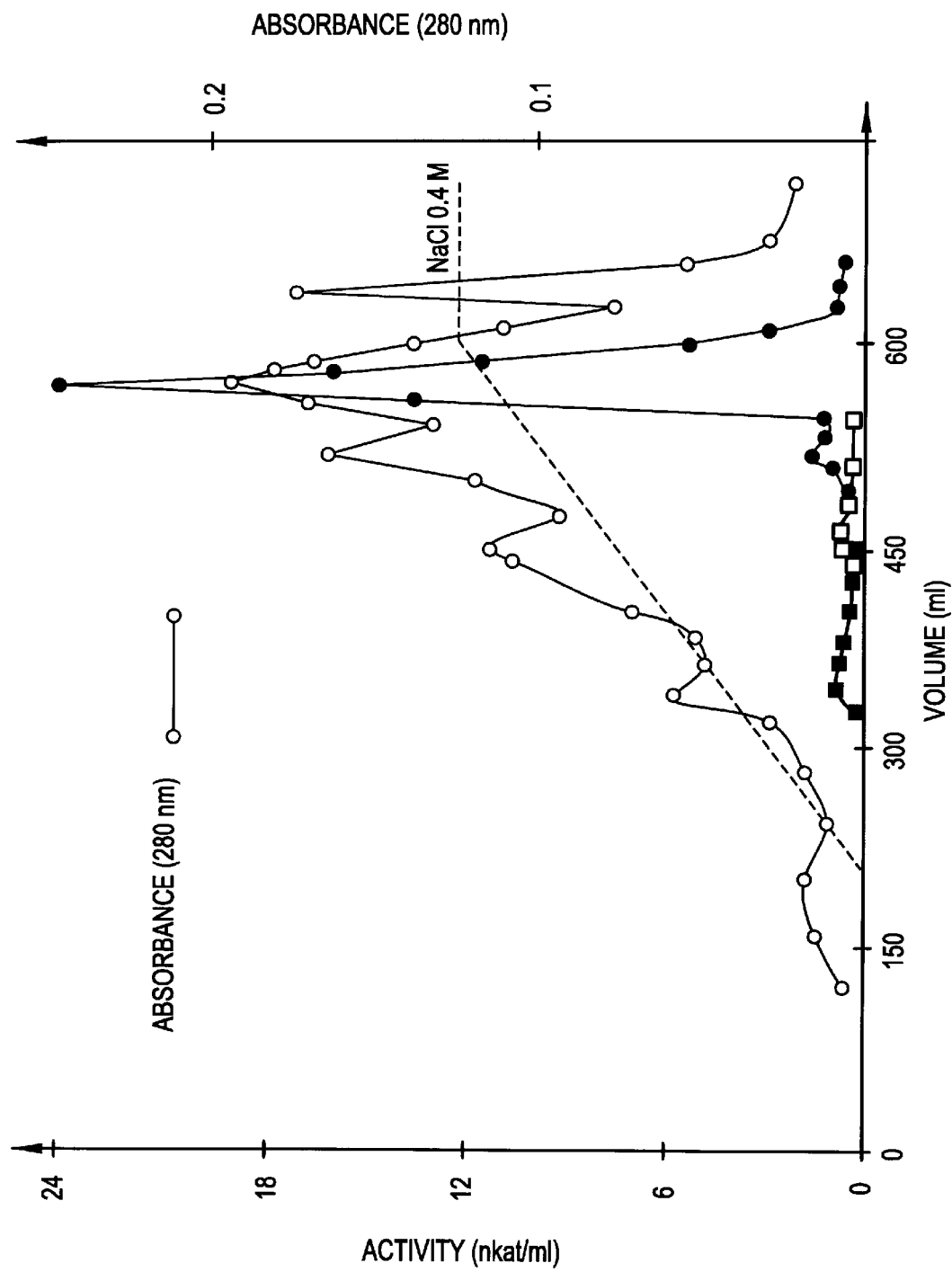
FIG. 3 shows a chromatographic profile of the ion exchange chromatography on DEAE-sepharose CL-6B of the α-arabinosidase fraction derived from the molecular sieving fractionation.

The chromatographic profile is shown in FIG. 3, the legend to which is as follows:

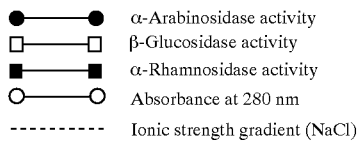

●————● α-Arabinosidase activity
□————□ β-Glucosidase activity
■————■ α-Rhamnosidase activity
○————○ Absorbance at 280 nm
---------- Ionic strength gradient (NaCl)

Under these conditions, the three activities are well separated. The peak eluted (69 ml) using 0.3M NaCl and corresponding to the α-arabinosidase activities (365 nkat) now contains only low β-glucosidase (0.43 nkat) and α-rhamnosidase (0.32 nkat) activities, equivalent to 0.1% (β-glucosidase) and 0.08% (α-rhamnosidase) relative to the α-arabinosidase activity.

It should be noted that, on completion of this stage, the α-arabinosidase fraction contains much less protein than the initial enzyme solution.

This stage enables the α-arabinosidase activity to be purified approximately 14-fold. However, since the presence of low β-glucosidase and α-rhamnosidase activities can interfere in the hydrolysis of natural and synthetic glycosides, the purification was refined by the application of a further (affinity) chromatographic technique.

Affinity Chromatography on Concanavalin A-Ultrogel of the α-arabinosidase Fraction Derived from the Chromatographic Stage of DEAE-Sepharose CL-6B Fractination The α-arabinosidase fraction (69 ml) is concentrated in a dialysis bag covered with Sephadex G-200 gel (pharmacia) to 12 ml. It is dialysed first against a 50 mM Tric-HCl buffer (pH 7.2) containing 0.1 M NaCl and 0.1 mM $MnCl_2$ overnight (+5° C.), and then injected onto a concanavalin A-UG gel (IBF, France) (1.0×10 cm), equilibrated beforehand with the above buffer, at a flow rate of 30 ml/h. The column is eluted with methyl α-D-mannopyranoside (Serva, FRG) in the same buffer, first with a linear gradient (0→15 M) and then isocratically (0.15 M). 1.5-ml fractions are collected, on which the optical density and the α-arabinosidase, β-glucosidase and α-rhamnosidase activities are measured. The combined fractions displaying α-arabinosidase activities are dialysed against 100 mM acetate buffer (pH 4.2) over-night (+4° C.) to remove the methyl α-D-mannopyranoside.

Results

Figure 4:
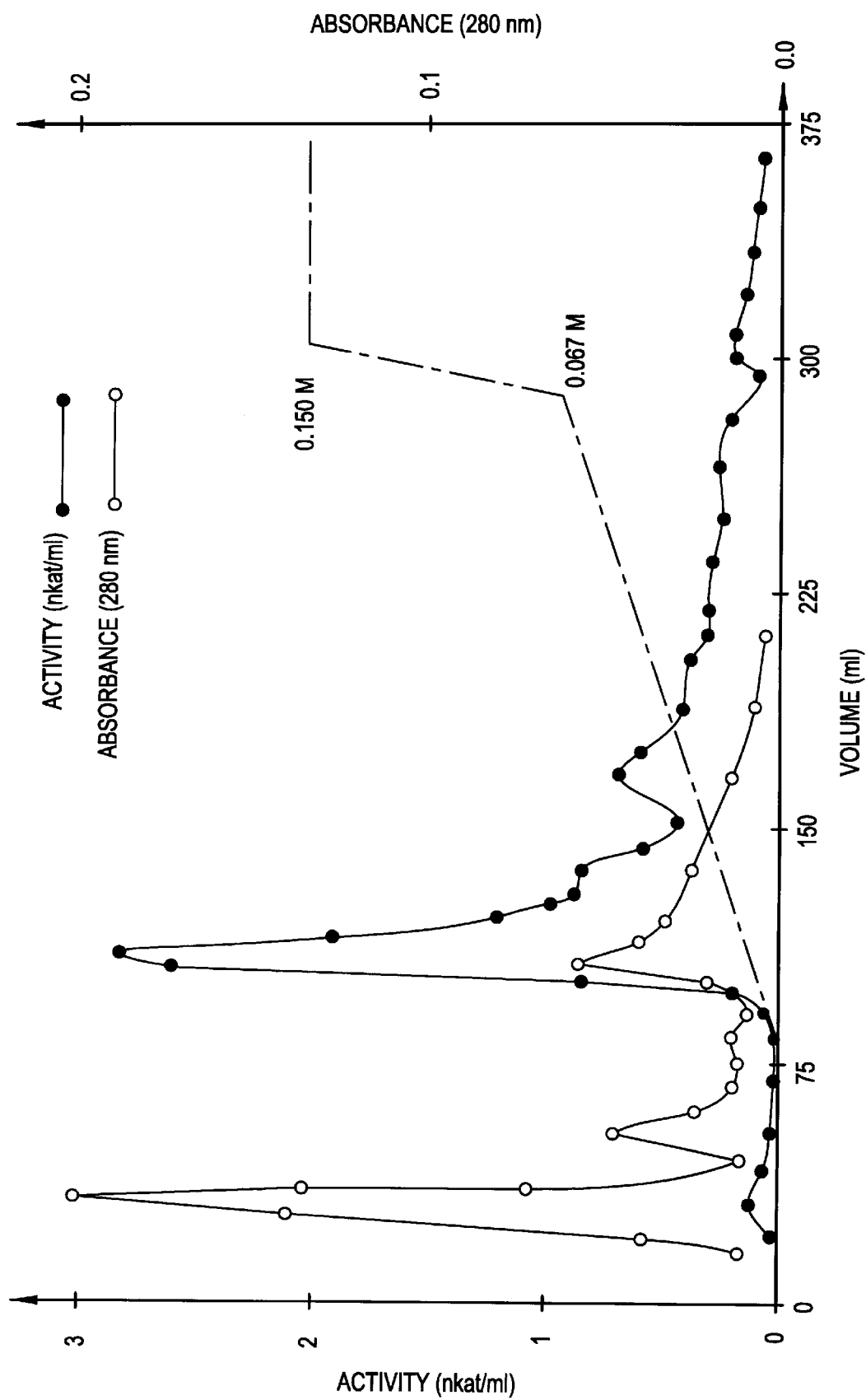
FIG. 4 shows a chromatographic profile of affinity chromatography on concanavalin A-Ultrogel of the α-arabinosidase fraction derived from the chromatographic stage on DEAE-sepharose CL-6B.

The chromatographic profile is shown in FIG. 4, the legend to which is as follows:

●————● α-Arabinosidase activity
○————○ Absorbance at 280 nm
————— Methyl α-D-mannopyranoside gradient This stage has made it possible to remove a majority of the proteins and all the residual β-glucosidase and α-rhamnosidase activities, verified after concentration of the fractions by dialysis against dry Sephadex G-200 gel. The major α-arabinosidase peak (17 ml; 75 nkat) represents 20.5% of the initial activity injected (365 nkat). A part of the activity (62.5 nkat) trails on elution with methyl α-D-mannopyranoside and corresponds to 17.1% of the initial activity. The enzyme was strongly bound to the gel, and the methyl α-D-mannopyranoside enabled only 37.6% of the initial activity to be eluted (similar results are observed for other enzymes).

As a result of this final stage, the α-arabinosidase activity has been purified approximately 27-fold. The enzyme solution used in the hydrolysis tests contains 29.9 nkat/ml of activity.

The numerical results corresponding to the different stages during the purification of α-arabinosidase from Hemicellulase are collated in Table 1.

TABLE 1

Purification of α-arabinosidase from Semicellulase REG-2

| Stage | Volume (ml) | Total activity (nkat) | Activity yield (%) | Total proteins (1) (mg) | Protein yield (%) | Specific activity (nkat mg$^{-1}$) | Purification factor |
|---|---|---|---|---|---|---|---|
| Crude Semi-cellulase (250 mg) | 3.2 | 2327 | 100 | 322.4 | 100 | 7.2 | 1 |
| Sieving on Ultrogel AcA 44 | 52 | 1759 | 75.6 | 112.3 | 34.8 | 15.7 | 2.2 |
| Ion exchange on DEAE-Sepharose Cl-68 | 69 | 365 | 15.7 | 3.6 | 1.1 | 101.3 | 14.1 |
| Affinity on Concanavalin A-Ultrogel | 34 | 75 | 3.2 | 0.4 | 0.1 | 192.3 | 26.7 |

(1)Proteins are assayed according to Lewry et al. (1951) "Protein measurement with the Folin phenol reagent", J. Biochem, 193, pages 265–275

Properties of the Purified α-arabinosidase pH Optimum

Figure 5A:
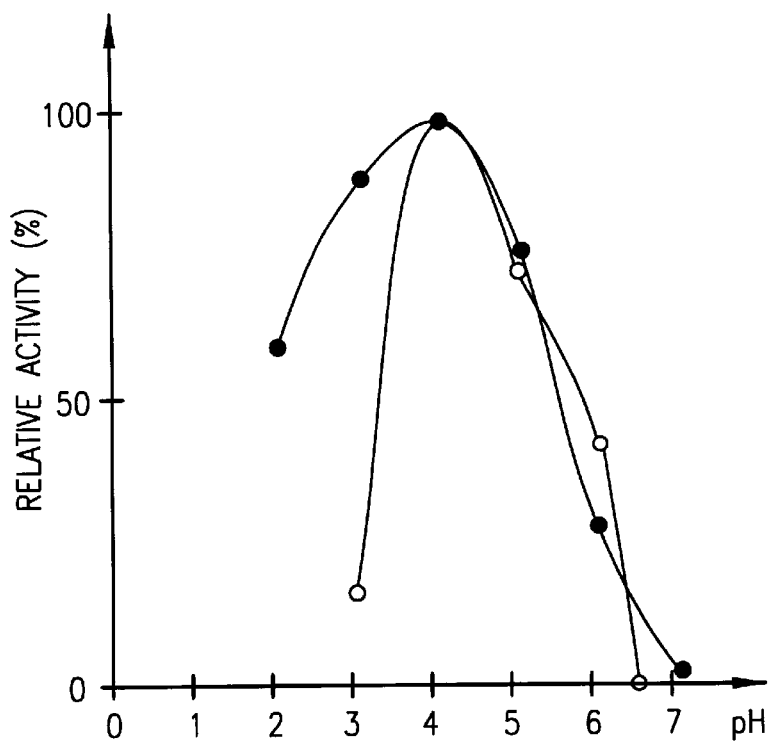
FIG. 5a shows the residual activity of purified α-arabinosidase as a function of pH.

The enzyme solution is incubated in the presence of its substrate (Ara-pNP) in universal buffer (Britton and Robinson type) of pH varying from 3.0 to 7.0. The activity measurements are carried out at the various incubation pH values under the conditions described at the beginning of this section A. The residual activity as a function of the pH is shown in FIG. 5a (curve ●————● ).

The α-arabinosidase activity is maximal at around pH 3.7–4.0.

Stability of the Activity as a Function of the pH

The enzyme solution is incubated for 50 min at 60° C. in a universal buffer whose pH varies from 3.0 to 6.5. The samples are then dialysed against 1 l of 100 mM acetate buffer (pH 4.2) for 5 hours (+5° C.). The residual activity measured is shown in FIG. 5a (curve ○————○ ).

The α-arabinosidase activity is relatively stable between pH 3.8 and 4.9. This stability decreases rapidly at pH values below 3.5 and above 5.5.

Temperature Optimum

The α-arabinosidase activity is determined after incubation of the reaction medium at different temperatures varying from 5° C. to 80° C. The relative activity as a function of the incubation temperature is shown in FIG. 5b (curve ●———● ).

The activity is maximal at 60° C.

Thermal Stability

Figure 5B:
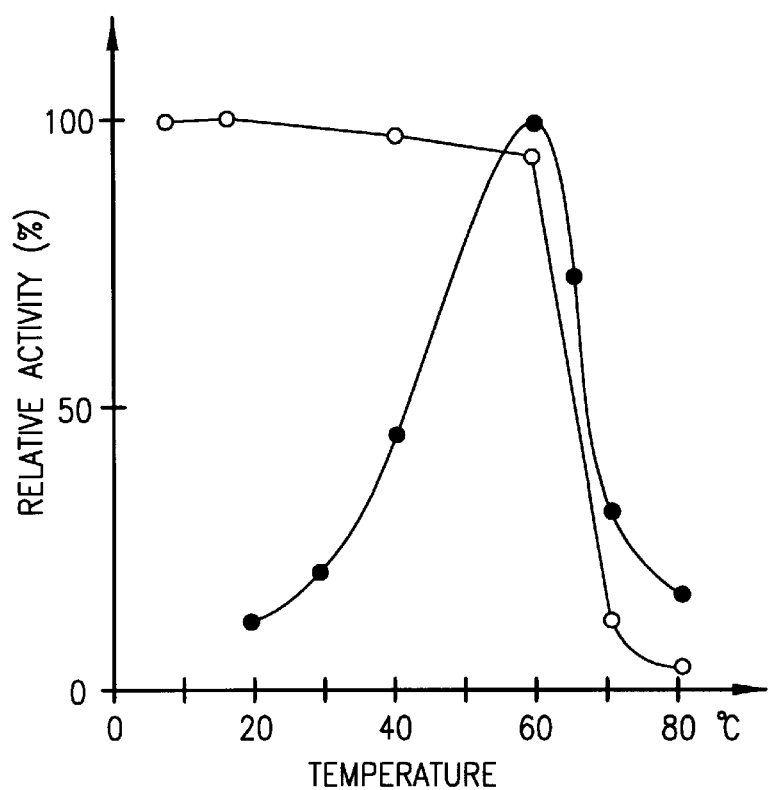
FIG. 5b shows the relative activity of α-arabinosidase as a function of the incubation temperature.

The enzyme solution is maintained at different temperatures (from 5° C. to 80° C.) in 100 mM acetate buffer (pH 4.2) for 30 minutes: the residual activity is then measured and the results are shown in FIG. 5b (curve ○———○ ).

The α-arabinosidase activity is stable up to 60° C., and above this the stability decreases abruptly. It is almost totally inactivated after a treatment at 70° C. for 30 minutes.

C. ENZYMATIC HYDROLYSES

The separate or sequential action of three enzymes, an α-L-arabinofuranosidase (E.C.3.2.1.55, designated α-arabinosidase), an α-L-rhamnopyranosidase (E.C.3.2.1.40, designated α-rhamnosidase) and a β-D-glucopyranosidase (E.C.3.2.1.21, designated β-glucosidase) was studied on different glycosidic substrates. The latter are, on the one hand p-nitrophenyl or geranyl α-L-rhamnopyranosyl-(1-→6)-β-D-glycopyranosides designated Rha-Glc-pNP or Rha-Glc-Ger) and p-nitrophenyl α-L-arabinofuranosyl-(1-→6)-β-D-glucopyranoside (designated Ara-Glc-pNP), and on the other hand a glycosidic extract purified from a muscat must.

It should be noted that the three synthetic glycosides studied possess the same structures in respect of their carbohydrate portion as the grape terpene glycosides, but differ in their aglycone which, for two of them, is p-nitrophenol (pNP).

The enzymatic hydrolysis is followed by thin-layer chromatography (TLC) and by gas chromatography (GC).

Thin-layer Chromatography (TLC)

Thin-layer adsorption chromatography was carried out on pieces of aluminum foil covered with a thin layer (0.2 mm) of silica gel (5553 Silica gel 60 without a fluorescence indicator, Merck). An ethyl acetate/isopropanol/water (65:30:10 v/v/v) mixture was used as a migration solvent.

The sugars and the glycosides are visualized by means of the following mixture, prepared immediately before use: 0.2% napthoresorcinol in ethanol/concentrated sulphuric acid (19:1 v/v). The application of this visualizing agent is followed by drying the plates in the oven (105° C.) for 15 minutes. Apart from their migration distance, the various compounds are also distinguished by their color. The glycosides are purple-red, the arabinosides are bluish, rhamnose greenish pink, arabinose blue and glucose pink.

Moreover, TLC enabled the portion of the glycosidic extract not hydrolysed by the enzymes to be recovered. The zone of the chromatographic plate where the corresponding spot is localized was scrapped off, the silica gel recovered and suspended in 50 ml of methanol. After being left overnight with gentle stirring, the suspension is filtered on a Büchner funnel and the gel is washed with 3×10 ml of methanol. The organic eluates are combined, taken to dryness under vacuum at 40° C. and then taken up in 500 μl of ultrapure water. The aqueous sample thereby obtained is then ready for acid hydrolysis.

Gas Chromatography (GC)

This technique was used in order to analyse both the sugars and the terpene glycosides and also the free terpenols. For this purpose, two different chromatographic systems were employed.

GC of the Glycosides

Glycosides and sugars are non-volatile compounds, and are hence not suited, as such, to an analysis by GC. It is essential to convert them to volatile compounds by means of a selected reagent. Trimethylsilyl derivatives therefore were formed, according to the following protocol:

40 μl of glycosidic extract and 60 μl of a solution of Glc-pNP (internal standard) at a concentration of 50 mg/l in ethyl acetate are introduced into a suitable flask. The mixture is taken to dryness at 40° C. with a stream of nitrogen. 40 μl of the silylating reagent (Tri-sil, Pierce, Rockford, Ill., USA) are then introduced; the flask is sealed and maintained at 40° C. for 20 minutes. After rapid cooling, the silylated sample is then ready for analysis by GC.

The apparatus used consists of a Series 30C gas chromatograph, an "on-column" injector (injected volume 0.5 μl) and a flame ionization detector (Girdel, France). A thin film (0.20 μm) of an OV-1 (girdel) apolar silicone phase is grafted onto the inner wall of the capillary column (50×0.32 mm I.D.). The oven temperature is programmed from 125 to 305° C. at the rate of 5° C./minute, then maintained at 305° C. for 15 minutes. Finally, the detector temperature is set at 300° C. and hydrogen is used as the carrier gas at a pressure of 120 kPa.

GC of the Terpenols

The monoterpene alcohols studied here are sufficiently volatile to be chromatographed as they are. To the pentane extract containing them, the internal standard, 4-nonanol (for synthesis, Merck, Darmstadt, FRG) is added in the proportion of 1 μl of a solution at a concentration of 2.89 mg/ml in pentane per 50 μl of medium. The mixture is then dried over sodium sulphate, filtered through glass wool and then concentrated to a volume in the region of 100 μl. For this purpose, the pentane is first removed using a conventional still, and then a Dufton type column of a size suited to the volume remaining to be concentrated.

The constituents of the concentrated extract are separated using a capillary column (25 m×0.32 mm I.D.) containing a CP wax 52 CB (Chrompack, Middelburg, Netherlands) polar phase. The grafted polyethylene glycol film was selected thick (1.28 μm) in order to permit the injection of large sample volumes, up to 4 μl. The analysis is performed using a Fractovap Series 2900 (Carlo Erba, Milan, Italy) chromatograph, equipped with a flame ionization detector maintained at 250° C. and an "on-column" injector. Hydrogen was used as the carrier gas at a pressure of 60 kPa, and the oven temperature was programmed as follows: isothermal at 70° C. for 5 minutes, followed by a rise to 195° C. at the rate of 2° C./minute and a plateau at 195° C. for 15 minutes.

High Performance Liquid Chromatography (HPLC)

Figure 10:
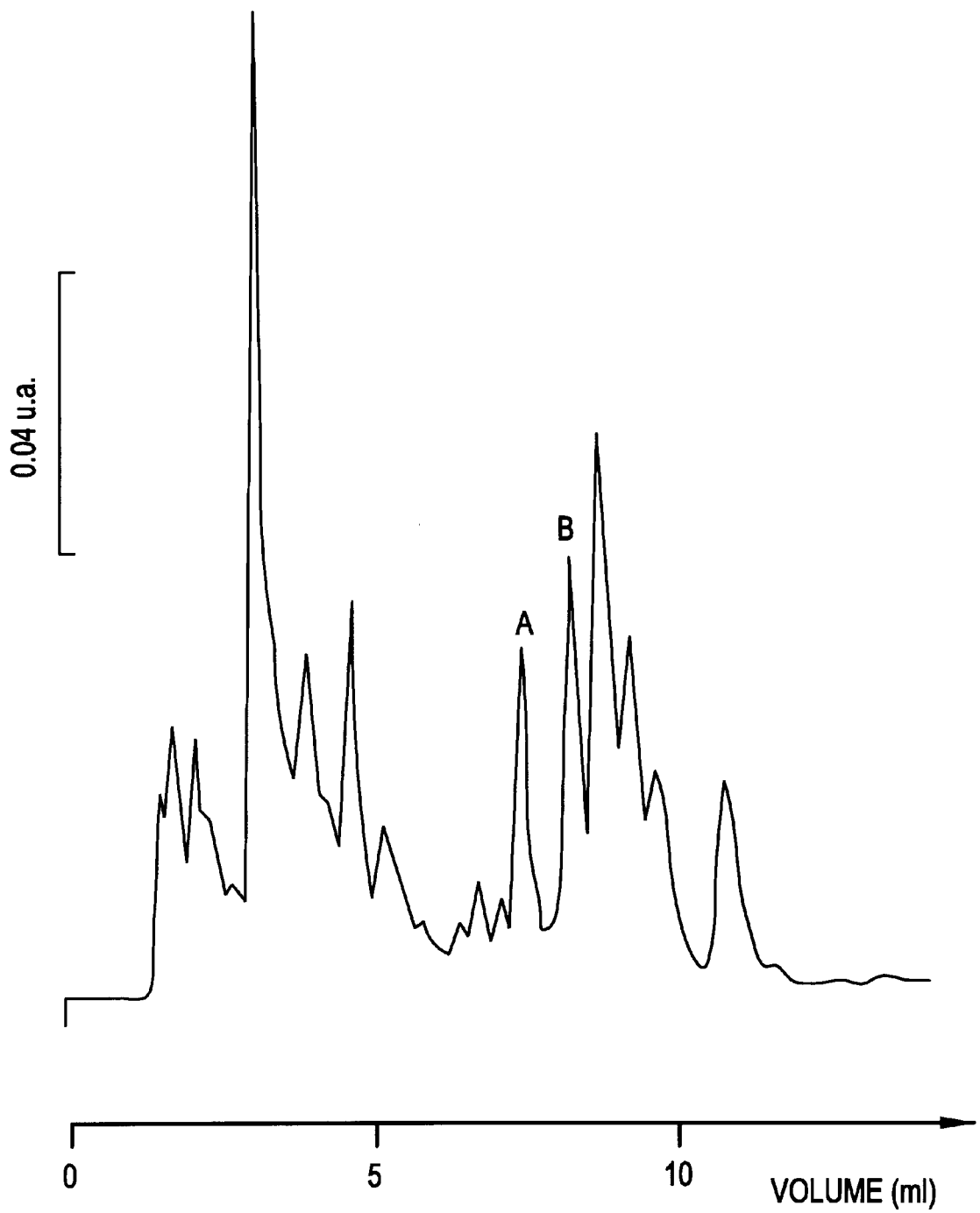
FIG. 10 shows the HPLC profile of the glycosidic extract.

The benefits of high performance liquid chromatography were exploited for isolating some terpene glycosides. For this purpose, fractions were collected as they emerged from the chromatographic system (more especially on elution of the peaks A and B) during the separation of the constituents of the glycosidic extract. (FIG. 10 below). Fifteen successive injections of 20 μl each enabled sufficient material to be isolated for the enzymatic hydrolyses and the analyses by GC to be performed in order to identify the compounds in question.

The chromatographic system consists of the following components: a Vista 5500 chromatograph equipped with a variable wavelength UV/visible spectrophotometer (Varian Assoc., Sunnyvale, Calif., USA); a six-way injection valve (Valco) equipped with a 20-µl loop; a stainless steel column (220×4 mm I.D.) filled with Spheri-5 (Brownlee Labs., Santa Clara, Calif., USA) octadecyl grafted silica of small particle size (5 µm); as well as a precolumn (37×4 mm I.D.) packed with the same stationary phase.

The chromatography is carried out using a water-/acetonitrile aqueous-organic mobile phase (reversed-phase polarity chromatography) and an elution graduated according to an increase in the acetonitrile content from 30 to 40% (by volume) in the course of 10 minutes. The elution solvent is pumped at a flow rate of 1 ml/min. The detection is performed at 200 nm and 0.5 absorbance unit full-scale.

1-Enzymatic Hydrolyses on Synthetic Substrates

In all the tests relating to the enzymatic hydrolysis of the synthetic substrates, the same glycosidase activity (0.15 nkat) is used for each of the enzymes (α-arabinosidase, α-rhamnosidase, β-glucosidase).

The hydrolysis and analysis protocols are given in plan form (Table 2).

The main abbreviations used will be recalled here:

| | |
|---|---|
| pNP | p-nitrophenol |
| Ara-pNP | p-nitrophenyl α-L-arabinofuranoside |
| Rha-pNP | p-nitrophenyl α-L-rhamnopyranoside |
| Rha—Glc-pNP | p-nitrophenyl α-L-rhamnopyranosyl-(1--> 6)-β-D-glucopyranoside |
| Rha—Glc—Ger | geranyl α-L-rhamnopyranosyl-(1--> 6)-β-D-glucopyranoside |
| Ara—Glc-pNP | p-nitrophenyl α-L-arabinofuranosyl-(1--> 6)-β-D-glucopyranoside |
| Ara—Glc—Ner | neryl α-L-arabinofuranosyl-(1--> 6)-β-D-glucopyranoside |
| Ara—Glc—Ger | geranyl α-L-arabinofuranosyl-(1--> 6)-β-D-glucopyranoside |
| Glc-pNP | p-nitrophenyl β-D-glucopyranoside |
| Glc—Lin | linalyl β-D-glucopyranoside |
| Glc—Ner | neryl β-D-glucopyranoside |
| Glc—Ger | geranyl β-D-glucopyranoside |

Figure 6B:
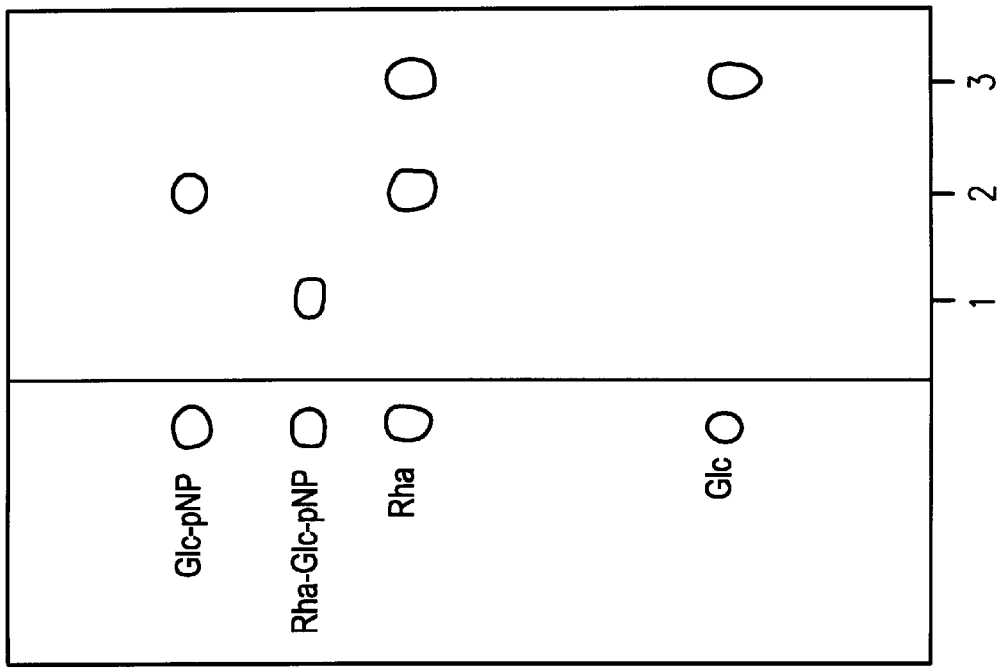
FIGS. 6a–6b show the TLC monitoring of the enzymatic hydrolysis of Ara-Glc-pNP (a) and Rha-Glc-pNP (b)
Figure 6A:
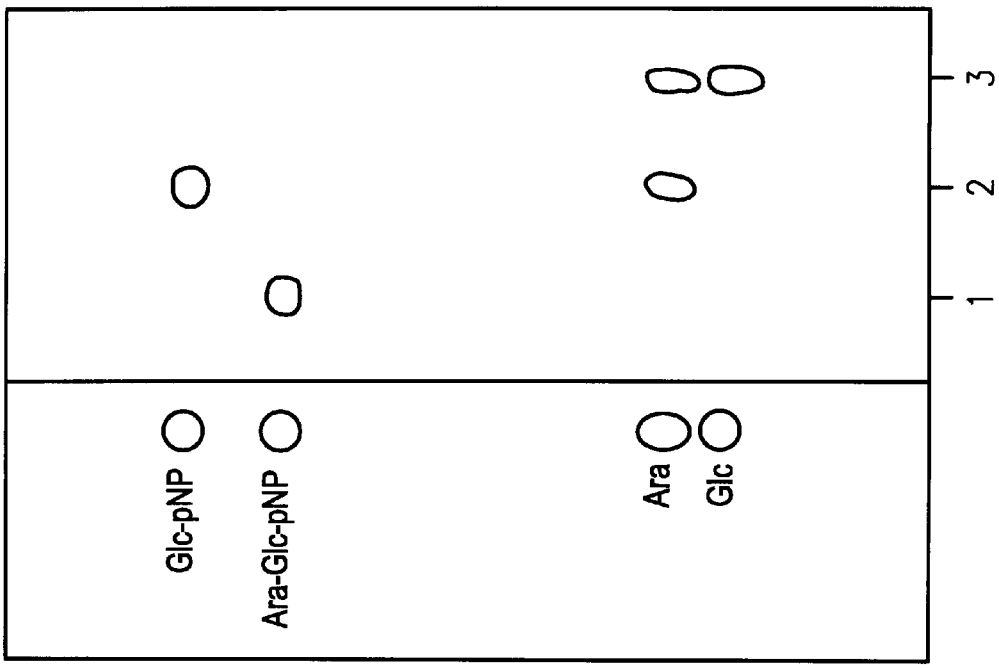

The results obtained in TLC are shown in FIG. 6, to which the legend is as follows:

Monitoring by TLC of the Enzymatic Hydrolysis of Ara-Glc-pNP (a) and Rha-Glc-pNP (b)

1a. Ara-Glc-pNP+β-glucosidase
2a. Ara-Glc-pNP+α-arabinosidase
3a. Ara-Glc-pNP+α-arabinosidase+β-glucosidase
1a. Rha-Glc-pNP+β-glucosidase
2a. Rha-Glc-pNP+α-rhamnosidase
3a. Rha-Glc-pNP+α-rhamnosidase+β-glucosidase The action of β-glucosidase on the different synthetic substrates gives rise to no modification.

The action of the α-arabinosidase on Ara-Glc-pNP causes the disappearance of this substrate and the appearance of arabinose and Glc-pNP.

Similarly, the action of α-rhamnosidase on Rha-Glc-pNP or Rha-Glc-Ger gives rise to the disappearance of these substrates and the appearance of rhamnose and Glc-pNP or Glc-Ger.

This constitutes the first stage of the hydrolysis.

The consecutive action of β-glucosidase on each of these media previously incubated with α-arabinosidase or α-rhamnosidase leads to the disappearance of Glc-Ger and Glc-pNP and the appearance of glucose (second stage).

As regards the corresponding aglycones (pNP or geraniol), they are liberated only after the sequential action of both glycosidases: α-rhamnosidase or α-arabinosidase, and then β-glucosidase.

These results show that the enzymatic hydrolysis of the glycosides studied proceeds well with the two stages described above.

2-Enzymatic Hydrolysis of a Glycosidic Extract Protocol for Production of the Glycosidic Extract The glycosidic extract was obtained by extraction of a must of Muscat de Frontignan variety grapes collected at maturity in the vines of the Station Experimentale de Pech Rouge (INRA Gruissan, France), followed by removal of the free terpenols and sugars.

In view of the large number of experiments to be carried out, it was essential to have recourse to a supply of glycoside which was consistent. To this end, the procedure was per-

TABLE 2

Plan of the protocol for enzymatic hydrolysis of the synthetic substrates*

| | 1st Stage | 2nd Stage | |
|---|---|---|---|
| 200 µl of 4 mM Ara—Glc-pNp in 100 mM acetate buffer (pH 4.2) | Addition of either 50 µl of a solution of α-arabinosidase (0.15 nkat) (TEST I) or 50 µl of a solution of β-glucosidase (0.15 nkat) (TEST II) | Incubation 40° C., 90 min then 12 µl --> TLC 30 µl --> pMP liberated | Addition of 50 µl of a solution of β-glucosidase (0.15 nkat) to TEST 1 Reincubation 40° C., 90 mins, then 15 µl --> TLC 36 µl --> pNP liberated |
| 200 µl of Rha—Glc-pNp (4 mN) or of Rha—Glc—Ger (solution not titrated) in 100 mN acetate buffer (pH 4.2) | Addition of either 50 µl of a solution of α-rhamnosidase (0.15 nkat) (TEST III) or 50 µl of a solution of β-glucosidase (TEST IV) | Incubation 40° C., 90 min then extraction with pentane (5 × 250 µl) --> GC 12 µl --> TLC 30 µl --> pNP liberated | Addition of 50 µl of a solution of β-glucosidase (0.15 nkat) to TEST III Reincubation 40° C., 90 min, then extraction with pentane (5 × 250 µl) - GC 15 µl - TLC 36 µl - pNP liberated |

*The controls are carried out under the same conditions, in the presence of the inactivated enzymes (95° C., 30 minutes)

formed on a large volume (80 liters) of previously centrifuged and sulphite-treated (50 ppm) must, and the extraction of the glycosidic material was carried out using 80 grams of active charcoal traditionally used in cenology (charcoal type CXV; Ceca S.A., Velizy-Villacoublay, France). The mixture was kept stirred for 4 hours and then left standing overnight. The charcoal was then recovered by filtration through cellulose filters (porosity 40–50 μm).

In order to remove the majority of the sugars also extracted by the charcoal, the latter was washed with 4×150 ml of water and filtered on a Büchner funnel. Monitoring by TLC enabled it to be verified that the sugar content decreased at each stage without elution of the glycosides taking place. The latter were then recovered by washing with 5×200 ml of acetone. Here too, monitoring by TLC enabled the quantitative elution of the glycosidic material to be checked. The acetone was removed by evaporation under vacuum and the sample was taken up in 40 ml of ultrapure water. A more exhaustive purification of the glycosidic extract was then carried out by fractionation on an Amberlite XAD-2 (Rohm & Haas Co., Philadelphie, Calif., USA) organic resin prepared according to the following protocol: grinding and sieving of the particles of size corresponding to a sieve of mesh aperture 175–350 μm (between 80 and 40 mesh), followed by three washes in a Soxhlet with methanol, acetonitrile and diethyl ether, in that order, for 8 hours for each solvent. The fractionation process, developed at the Laboratoire des Aromes et des Substances Naturelles (Aromas and Natural Substances Laboratory), has already been described in detail. In this study, it was applied twice consecutively, and comprised the following stages:

a resin, suspended in methanol, is poured into a glass column (35×1 cm) terminating in a Teflon tap and a glass wool plug. After settling, the resin layer measures approximately 20 cm. Several 50-ml portions of methanol are then passed through, followed by washing with 50 ml of diethyl ether and finally equilibration of the resin using 100 ml of ultrapure water. The column is then ready for use.

The 40 ml of glycosidic extract are passed through the column at a flow rate of between 2 and 2.5 ml/minute. The column is then washed with 100 ml of water to remove residual sugars, and with 100 ml of pentane in order to elute the free terpenols bound by the resin, the flow rate being the same as above.

The glycosides are then recovered by elution using 100 ml of ethyl acetate. The composition of this fraction is studied by TLC, which enables the absence of free sugars to be verified (in this instance, at the end of the second fractionation on XAD-2).

The glycoside fraction was taken to dryness under vacuum and then taken up in 18 ml of water. The glycosidic extract used in the chromatographic and enzymatic experiments was thereby obtained.

Hydrolysis

The experimental protocols for the enzymatic hydrolysis on the glycosidic extract are collated in Table 3.

TABLE 3

Plan of the protocol for enzymatic hydrolysis of the glycosidic extract*

| | 1st Stage | | 2nd Stage |
|---|---|---|---|
| 200 μl of glycosidic extract** | Addition of either 50 μl of a solution of α-arabinosidase (0.15 nkat) (TEST I) or 50 μl of a solution of α-rhamnosidase (0.15 nkat) (TEST II) OR 50 μl of a solution of β-glucosidase (0.15 nkat) (TEST III) | Incubation 40° C., 16 h then Extraction with pentane (5 × 250 μl) --> GC 50 μl aqueous phase silylation --> GC 12 μl aqueous phase --> TLC | ADDITION of 50 μl of a solution of β-glucosidase (0.15 nkat) to TEST I and II Reincubation 40°, 16 h then Extraction with pentane (5 × 250 μl) --> GC 65 ml aqueous phase --> silylation --> GC 15 μl aqueous phase --> TLC |

*The controls are carried out under the same conditions, in the presence of the inactivated enzymes (95° C., 30 minutes).
**Before the enzymatic hydrolyses, the glycosidic extract is washed again several times with pentane in order to remove traces of terpenols.

Figure 7:
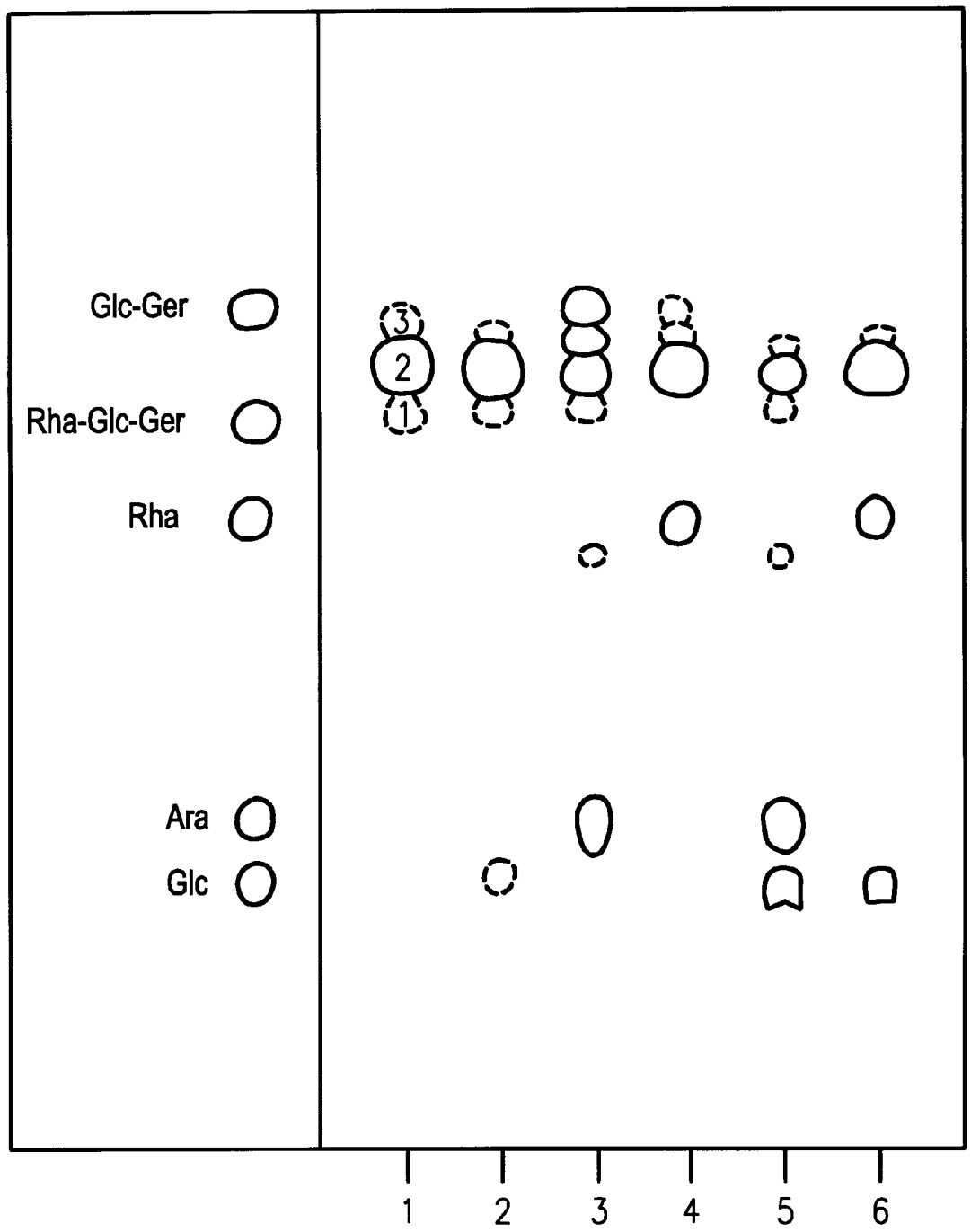
FIG. 7 shows the results of enzymatic hydrolysis of a glycosidic extract of a must of Muscat de Frontignan variety of grapes.

This hydrolysis is monitored by TLC and GC.
Monitoring of the Hydrolysis by TLC
The results are shown in FIG. 7:
Monitoring by TLC of the Enzymatic Hydrolysis of the Glycosidic Extract
1. Glycosidic extract
2. Glycosidic extract+β-glucosidase
3. Glycosidic extract+α-arabinosidase
4. Glycosidic extract+α-rhamnosidase
5. Glycosidic extract+α-arabinosidase+β-glucosidase
6. Glycosidic extract+α-rhamnosidase β-glucosidase The initial glycosidic extract shows a major spot (Rf 0.71, No. 2 on TLC) and two minor spots (RD 0.67 and 0.79, No. 1 and No. 3 on TLC).

The hydrolysis of this extract with β-glucosidase gives rise to a faint spot having the same Rf (0.26) as glucose, and reduces the larger spot (No. 3).

In the case of the hydrolysis with α-arabinosidase, a substantial reduction is observed in the major spot (No. 2), and the appearance is noted of spots having Rf values (0.76, 0.79) identical to those of the terpene monoglucosides and with the Rf (0.31) of arabinose, and of a faint unknown spot with an Rf (0.55) less than that of rhamnose.

When the glycosidic extract is subjected to the action of α-rhamnosidase, the spot No. 1 corresponding to the Rf of Rha-Glc-Ger disappears and a faint spot with the Rf of the terpene monoglucosides appears. In this case, only rhamnose (Rf 0.59) is to be found as the monosaccharide liberated.

The consecutive action of β-glucosidase on each of the media incubated with either α-arabinosidase or α-rhamnosidase substantially reduces the spots with the Rf of monoglucosides, and gives rise to glucose.

However, since the major spot (No. 2) of the glycosidic extract did not completely disappear after sequential action of the glycosidses, the remaining portion was recovered and then subjected to an acid hydrolysis, under the conditions described below, to see whether or not it contained terpenols. Its hydrolysis at pH 3.0 neither gave rise to modifications (verified by TLC) nor liberated terpenols (verified by GC). On the other hand, complete hydrolysis with 2 M trifluoroacetic acid caused this spot to disappear and liberated glucose, rhamnose and an unknown compound (Rf 0.55), but no terpenols (GC).

Thus, it was demonstrated that the spot which resists the conjugate action of the glycosidases does not contain terpene glycosides.

These TLC tests provided information about the fate of the carbohydrate portion of the glycosides during their hydrolysis with purified enzymes. It emerges from these results that the hydrolysis of terpene glycosides involves a sequential hydrolysis. The mechanism of this hydrolysis was demonstrated more precisely by GC analysis.

Monitoring of the Hydrolysis by GC

Figure 8A:
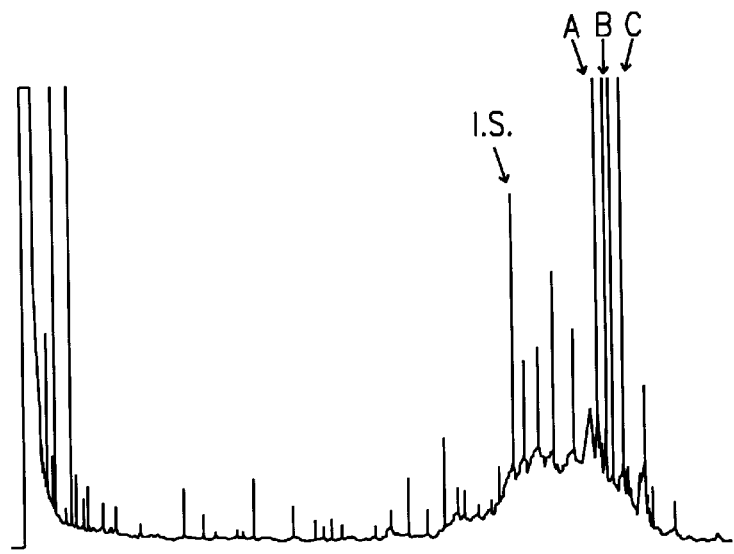
FIGS. 8a–8c show monitoring by gas chromatography of the enzymatic hydrolysis of the glycosidic extract.

At each stage of the hydrolysis, the reaction products (sugars, terpene glycosides and terpenols) are analysed by GC. The results are shown in FIGS. 8 and 9:

FIG. 8: Monitoring by GC of the Enzymatic Hydrolysis of the Glycosidic Extract
   a. Silylated glycosidic extract
   b. Glycosidic extract+α-arabinosidase
   c. Glycosidic extract+α-arabinosidase+β-glucosidase
   I.S. Internal Standard (Glc-pNP)
   1 and 2. α- and β-arabinose
   5 and 6. α- and β-glucose
   a. Glc-Lin
   b. Glc-Ner
   c. Glc-Ger
   A. Ara-Glc-Ner
   B. Ara-Glc-Ger FIG. 9: As FIG. 8, in the Case of the Sequential Hydrolysis by α-rhamnosidase+β-glucosidase
   3 and 4. α- and β-rhamnose The initial (silylated) glycosidic extract contains neither monosaccharides nor terpene monoglucosides (FIG. 8a).

The action of β-glucosidase does not substantially modify the profile of this extract, apart from the appearance of glucose. The latter, also observed by TLC during the monitoring of the hydrolysis of the glycosidic extract by this enzyme, hence probably does not originate from the hydrolysis of the terpene precursors, but from other glycosides.

Figure 8B:
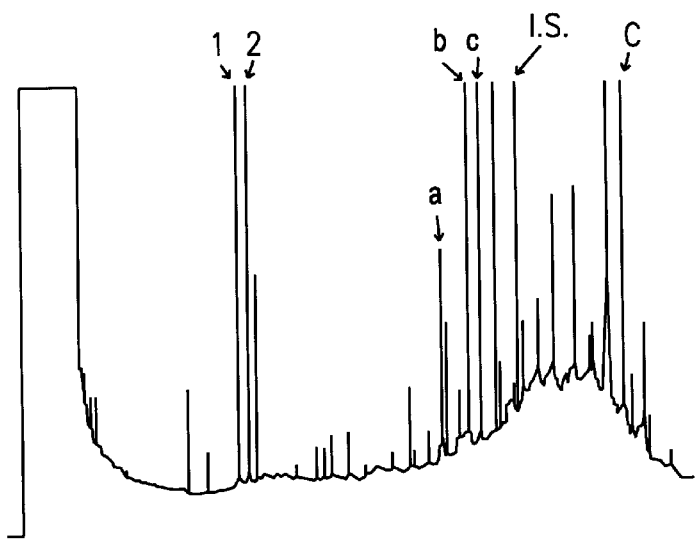
Figure 8C:
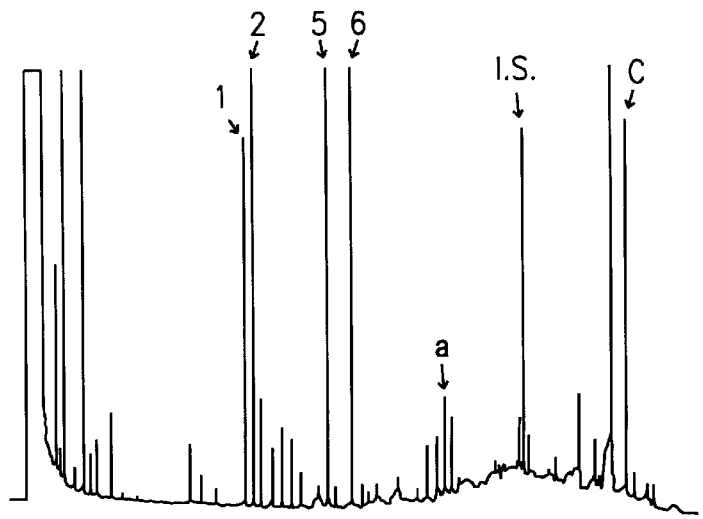
Figure 9A:
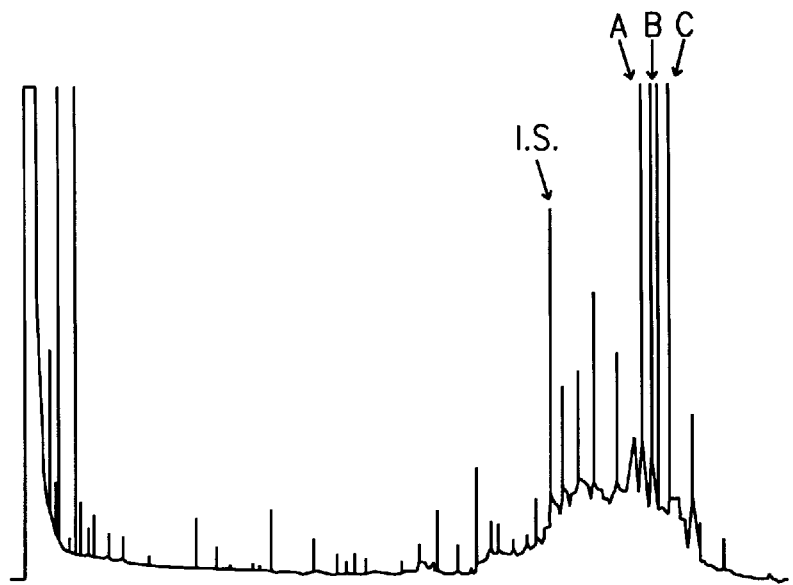
FIGS. 9a–9c show the sequential hydrolosis by α-rhamnosidase and β-glucosidase. The abbreviations are as shown in FIG. 8.
Figure 9B:
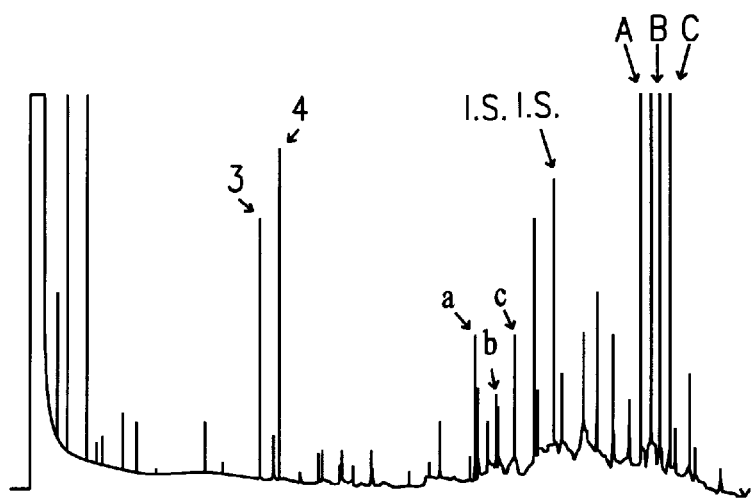
Figure 9C:
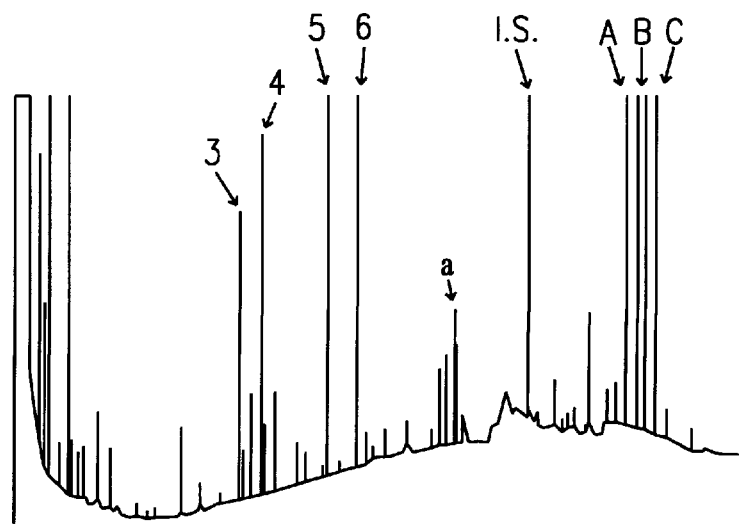

The action of α-arabinosidase or of α-rhamnosidase gives rise to substantial modifications with respect to the profile of the glycosidic extract (FIGS. 8b and 9b). In particular, the two major peaks which have been identified (peak A=Ara-Glc-Ner; peak B=Glc-Ger) disappear completely after incubation of the medium with α-arabinosidase, while arabinose appears. The peak C, corresponding to the retention time of Rha-Glc-Ger, decreases after the action of α-rhamnosidase; the appearance of rhamnose is observed simultaneously.

Incubation of the glycosidic extract with each of these two glycosidases, gives rise, moreover, to three abundant monoglucosides (linalyl, neryl and geranyl glucosides), identified by comparison with reference substances. The larger part (77%) of these terpene monoglucosides is liberated by the action of α-arabinosidase, the remainder (23%) produced by the action of α-rhamnosidase (Table 5).

TABLE 5

Terpene monoglucosides liberated[1] by α-arabinosidase and α-rhamnosidase from a glycosidic extract

|  | α-arabinosidase | α-rhamnosidase | % of monoglucosides |
|---|---|---|---|
| Glc—Lin | 10 | 9 | 19 |
| Glc—Ner | 28 | 5 | 33 |
| Glc—Ger | 39 | 9 | 48 |
| % of monoglucosides | 77 | 23 | 100 |

[1]The results are expressed as a percentage of the total amount of each compound liberated by the two enzymes.

The amounts of terpenols detected during this first stage of the hydrolysis, namely the hydrolysis of the glycosidic extract with each of the three glycosidases alone, were only negligible.

The consecutive action of β-glucosidase on the glycosidic extracts previously incubated either with α-arabinosidase or α-rhamnosidase (second stage) gives rise to the disappearance of the neryl and geranyl monoglucosides and a reduction in the linanyl monoglucoside, and the production of glucose (FIGS. 8c and 9c) and terpenols in large amounts.

It is assumed that the β-glucosidase used, which is extracted from sweet almond and selected for the purpose of studying the sequential hydrolysis of terpene glycosides, has a low affinity with respect to linalyl glucoside, resulting in incomplete hydrolysis of the latter under the conditions used.

The most abundant of the terpenols liberated are geraniol, nerol and linalool, in that order. Approximately 80% of these terpenols are derived from the conjugate action of α-arabinosidase an β-glucosidase.

Other terpenols or volatile compounds have also been detected, but in small amounts, after the sequential action of the enzymes, such as α-terpineol, citronellol, linalool oxides (with the cis and trans furan configurations and the cis pyran configuration) and benzyl and phenyl ethyl alcohols.

The substantial modifications of the chromatographic profiles observed after the action of α-arabinosidase on the glycosidic extract led to an investigation in greater depth of the preponderant glycosides. For this purpose, fractions corresponding to the peaks A and B of the HPLC profile were collected. An aliquot portion was silylated and then analysed by GC. The correspondance between the peaks A and B of the two chromatograms of FIGS. 10 and 8a was thus established.

Legend to FIG. 10:
   HPLC profile of the glycosidic extract
   A. Ara-Glc-Ner
   B. Ara-Glc-Ger Furthermore, each fraction was subjected to the sequential action of α-arabinosidase and then β-glucosidase. At the end of each stage and according to the procedures described, the incubated medium was analysed by GC in order to test for sugars and glucosides on the one hand, and for terpenols on the other hand. The results are collated in Table 4. Thus, the peaks A and B were identified, respectively, as neryl and geranyl α-L-arabinofuranosyl-β-D-glucopyranosides. The identity of the geranyl glycoside was verified, in addition, by co-injection of the glycosidic extract with the synthetic compound.

TABLE 4

Identification of the peaks A and B collected by HPLC

| | Compounds appearing after action of | | |
|---|---|---|---|
| | α-arabino-sidase | α-arabinosidase and then β-glucosidase | Compounds identified |
| Peak A | arabinose + Glc—Ner | glucose + nerol | neryl β-L-arabino furanosyl-β-D-glucopyranoside |
| Peak B | arabinose + Glc—Ger | glucose + geraniol | geranyl α-L-arabino furanosyl-β-D-glucopyranoside |

These results collectively confirm that the enzymatic hydrolysis of grape terpene glycosides involves a sequential mechanism identical to that demonstrated on the synthetic substrates.

3-Enzymatic Hydrolysis on Natural Media

The enzymatic hydrolysis of a glycosidic extract incorporated, on the one hand into a natural medium (must or dry wine), and on the other hand into a reference medium (buffer), by the action of commercial preparations containing the requisite three glycosidases, was studied.

The hydrolysis protocol is as follows:

A juice and a wine of a vine variety not containing terpenols and terpene glycosides, but enriched beforehand with a known amount of glycosidic extract of muscat, are treated with commercial enzyme preparations. The media, as well as controls, are incubated at 25° C. for 86 hours (see the experimental protocol plan below). They are then passed through a column of Amberlite XAD-2 according to the protocol applied for the production of the glycosidic extract, and the terpenols are assayed by GC.

Plan of the Experimental Protocol

| 50 ml must (pH 3.4: sugars 180 g/l) or | + 0.5 ml Hemicellulase(1) + 0.5 ml Naringinase(2) + 2 ml 2% NaN$_3$(3) | Control |
|---|---|---|
| Dry white wine (pH 3.1) | + 0.5 ml Hemicellulase + 0.5 ml Naringinase + 1 ml Glycosidic extract(4) + 2 ml 2% NaN$_3$ + 1 ml Glycosidic extract | |
| | | Control |
| 50 ml buffer (50 mM citrate-phosphate) pH 3.3 | + 2 ml 2% NaN$_3$ + 0.5 ml Hemicellulase + 0.5 ml Naringinase | |
| | | Reference |
| | + 1 ml Glycosidic extract + 2 ml 2% NaN$_3$ | |

(1) 0.5 ml of the solution (at a concentration of 15 mg/ml) of Hemicellulase REG-2 used possessed 70 nkat of α-arabinosidase activity, 72 nkat of β-glucosidase activity and 9 nkat of α-rhamnosidase activity.

(2) 0.5 ml of the solution (at a concentration of 5 mg/ml) of Naringinase used possessed 78 nkat of α-rhamnosidase activity and 0.1 nkat of β-glucosidase activity.

(3) NaN$_3$ is used in order to avoid microbial growth.

(4) The glycosidic extract used is obtained by passing a must of Muscat d'Alexandrie variety grapes through Amberlite XAD-2. The amount of glycosidic extract (1 ml) added in the tests corresponds to that found in 50 ml of must of Muscat d'Alexandrie variety grapes.

Under conditions resembling those found in œnological practice, a liberation of terpenols is observed. This liberation is smaller in the case of must than in that of wine (Table 6). In terms of the percentage of aroma liberated after 86 hours at 25° C. compared with the amount liberated in a reference medium, this comes to 11% for the must and 28% for the wine. It may be noted that geraniol glycosides are more satisfactorily hydrolysed than those of linalool and nerol.

It was shown that the inhibition of the β-glucosidase activity by the glucose present in large amounts in the must can explain the lower efficiency relative to the wine.

The results are more satisfactory in the case of wine, since it is then possible, taking into account the preponderance of terpene glycosides, to at least double the free terpene fraction.

TABLE 6

Hydrolysis of a glycosidic extract incorporated into a must and a wine by commercial enzyme preparations

| | Compounds liberated relative to the reference medium$^{(1)}$ (%) | | | | |
|---|---|---|---|---|---|
| | Linalol | Nerol | Geraniol | Benzyl alcohol | Total terpenols |
| MUST | 9 | 6 | 15 | 46 | 11 |
| WINE | 14 | 18 | 49 | 50 | 28 |

$^{(1)}$Reference: Glycosidic extract + citrate-phosphate buffer, 3.3 + Hemicellulase REG-2 + Naringinase.

Acid Hydrolyses

In order to detect the possible presence of terpene glycosides of unknown structure in the (TLC) spot resistant to enzymatic hydrolyses by the purified glycosidases, acid hydrolyses were applied to the compounds corresponding to this spot recovered by TLC.

1) The recovered medium (250 μl) is taken to dryness at 40° C. with a stream of nitrogen. 250 μl of 25 mM citrate-phosphate buffer (pH 3.0) are introduced into the flask, which is then sealed and left at 100° C. for 20 minutes. After being cooled, the medium is washed with pentane (5×250 μl). Internal standard is added to the pentane extract, which is then concentrated and analysed by GC. 25 μl of the aqueous phase are then placed on a TLC plate.

2) The recovered medium (250 μl), after being dried as above, is treated with 250 μl of 2 M trifluoroacetic acid and then left at 120° C. for 75 minutes. After being cooled, the medium is subjected to the same analyses as above.

We claim:

1. A method for obtaining aroma components and aromas from their glycosidic precursors, said method comprising:

in a first step hydrolysing a glycosidic substrate containing at least one of said precursors with at least one first enzyme which cleaves a glycosidic bond of said precursor and substantially reduces the amount of said precursor, whereby at least one monoglycoside product is obtained; and in a second step hydrolysing said monoglycoside product with at least one second enzyme other than said first enzyme, wherein said second enzyme cleaves an aglycone-carbohydrate linkage bond whereby said aroma components and aromas are obtained.

2. A method for obtaining aroma components and aromas from their glycosidic precursors, said method comprising:

hydrolysing a glycosidic substrate comprising only monoglycosides with at least one enzyme which cleaves an aglycone-carbohydrate linkage bond, whereby said aroma components and aromas are obtained.

3. The method according to claim 1, wherein said hydrolysing with said first and second enzymes is substantially simultaneous.

4. The method according to claim 1, wherein said glycosidic substrate is selected from the group consisting of:
1) a vegetable material derived from a fruit, an aromatic plant or a flowering plant;
4) a derivative of a fruit, an aromatic plant, or a flowering plant;
3) a by-product of a fruit, an aromatic plant or a flowering plant; and
4) a plant material originating from in vitro cell cultures.

5. The method according to claim 4, wherein said vegetable material is derived from grapes.

6. The method according to claim 5, wherein said vegetable material derived from grapes is selected from the group consisting of grape juice, wine, derivatives of grape juice or wine, and by-products of the vinification of aromatic vine varieties.

7. The method according to claim 1, wherein said glycosidic substrate comprises an extract of a must originating from an aromatic vine variety and wherein said extract is free of terpenols and sugars.

8. The method according to claim 1, wherein said glycosidic substrate is a natural medium.

9. The method according to claim 8, wherein said natural medium is juices and wines of a vine variety with the proviso that when said natural medium does not contain terpenols and terpene glycosides, said natural medium is enriched with a glycosidic extract derived from grape juice, wine, or derivatives of grape juice or wine, or by-products of the vinification of aromatic vine varieties.

10. The method according to claim 1, wherein said glycosidic substrate is a synthetic substrate.

11. The method according to claim 10, wherein said synthetic substrate is p-nitrophenyl α-L-rhamnopyranosyl-(1→6)-β-D-glucopyraoside, geranyl α-L-rhamnopyranosyl-(1→6)-β-D-glucopyranoside or p-nitrophenyl α-L-aribinofuranosyl-(1→6)-β-D-glucopyranoside.

12. A method for obtaining aroma components and aromas from their glycosidic precursors, said method comprising:

hydrolysing a glycosidic substrate containing at least one of said precursors with a first enzyme composition consisting essentially of an α-arabinosidase and an α-rhamnosidase, whereby at least one monoglycoside product is obtained and said at least one precursors is substantially reduced; and hydrolysing said product with at least one second enzyme composition consisting essentially of a β-glucosidase whereby said aroma components and aromas are obtained.

13. The method according to claim 12, wherein said α-arabinosidase and said α-rhamnosidase are an α-L-arabinofuranosidase (E.C.3.2.1.55) and an α-L-rhamnopyranosidase (E.C.3.2.1.40) respectively, and said β-glucosidase is a β-D-glucopyranosidase (E.C.3.2.1.21).

14. The method according to claim 1, wherein said aroma components or aromas consist essentially of at least one of geraniol, linalol, nerol phenyl ethyl alcohol or benzyl alcohol.

* * * * *